United States Patent
Gusarova et al.

(10) Patent No.: US 12,281,173 B2
(45) Date of Patent: Apr. 22, 2025

(54) METHODS FOR TREATING PATIENTS WITH HYPERLIPIDEMIA BY ADMINISTERING A PCSK9 INHIBITOR IN COMBINATION WITH AN ANGPTL3 INHIBITOR

(71) Applicant: Regeneron Pharmaceuticals, Inc., Tarrytown, NY (US)

(72) Inventors: Viktoria Gusarova, Pleasantville, NY (US); Jesper Gromada, Scarsdale, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 233 days.

(21) Appl. No.: 16/808,058

(22) Filed: Mar. 3, 2020

(65) Prior Publication Data
US 2020/0199253 A1    Jun. 25, 2020

Related U.S. Application Data

(63) Continuation of application No. 15/446,720, filed on Mar. 1, 2017, now abandoned.

(60) Provisional application No. 62/302,907, filed on Mar. 3, 2016.

(51) Int. Cl.
C07K 16/40 (2006.01)
A61K 9/00 (2006.01)
C07K 16/22 (2006.01)
A61K 39/00 (2006.01)

(52) U.S. Cl.
CPC ............ *C07K 16/40* (2013.01); *A61K 9/0019* (2013.01); *C07K 16/22* (2013.01); *A61K 2039/505* (2013.01); *A61K 2039/507* (2013.01); *A61K 2039/545* (2013.01); *C07K 2317/21* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,997,423 A | 3/1991 | Okunda et al. |
| 5,908,686 A | 6/1999 | Sudo et al. |
| 6,030,831 A | 2/2000 | Godowski |
| 6,286,699 B1 | 9/2001 | Sudo |
| 6,348,351 B1 | 2/2002 | Fong |
| 6,629,949 B1 | 10/2003 | Douglas |
| 6,645,635 B2 | 11/2003 | Muraki |
| 6,659,982 B2 | 12/2003 | Douglas et al. |
| 7,226,554 B2 | 6/2007 | Sudo et al. |
| 7,267,819 B2 | 9/2007 | Ferrara |
| 7,935,796 B2 | 5/2011 | Lee |
| 8,062,640 B2 | 11/2011 | Sleeman |
| 8,742,075 B2 | 6/2014 | Lee et al. |
| 9,018,356 B2 | 4/2015 | Sleeman et al. |
| 9,322,018 B2 | 4/2016 | Bettencourt |
| 9,951,127 B2 | 4/2018 | Sleeman et al. |
| 9,957,292 B2 | 5/2018 | Prakash et al. |
| 2002/0035058 A1 | 3/2002 | Brown et al. |
| 2008/0177045 A1 | 7/2008 | Lee |
| 2009/0098117 A1 | 4/2009 | Ferrara |
| 2010/0166768 A1 | 7/2010 | Sleeman et al. |
| 2011/0243948 A1 | 10/2011 | Lee |
| 2011/0245096 A1 | 10/2011 | Aggarwal |
| 2012/0064160 A1 | 3/2012 | Guivarc'h et al. |
| 2012/0135976 A1 | 5/2012 | Kerc et al. |
| 2013/0064834 A1 | 3/2013 | Sleeman |
| 2013/0171149 A1 | 7/2013 | Sleeman et al. |

(Continued)

FOREIGN PATENT DOCUMENTS

| CN | 101905024 | 12/2010 |
| CN | 107106678 A | 8/2017 |

(Continued)

OTHER PUBLICATIONS

Brown et al., "Tolerance of single, but not multiple, amino acid replacements in antibody VH 2: a means of minimizing B cell wastage from somatic hypermutation?", J. Immuno May 1996, 3285-91.

(Continued)

*Primary Examiner* — Sharon X Wen

(74) *Attorney, Agent, or Firm* — Merchant & Gould, P.C.

(57) ABSTRACT

The present invention provides methods for treating patients suffering from hypercholesterolemia, wherein the patient is non-responsive to, inadequately controlled by, or intolerant to treatment with a standard lipid modifying therapy. The methods of the invention provide for lowering at least one lipid parameter in the patient by administering a therapeutically effective amount of an antibody or antigen-binding fragment thereof that specifically binds to proprotein convertase subtilisin/kexin type 9 (PCSK9) in combination with a therapeutically effective amount of an antibody that specifically binds to angiopoietin-like protein 3 (ANGPTL3). The combination of an anti-PCSK9 antibody with an anti-ANGPTL3 antibody is useful in treating diseases such as hypercholesterolemia, including familial hypercholesterolemia (FH), both heFH and hoFH, as well as hyperlipidemia, hyperlipoproteinemia and dyslipidemia, including hypertriglyceridemia, chylomicronemia, and to prevent or treat diseases or disorders, for which abnormal lipid metabolism is a risk factor, such as cardiovascular diseases.

25 Claims, 8 Drawing Sheets

Specification includes a Sequence Listing.

(56) References Cited

U.S. PATENT DOCUMENTS

| | | |
|---|---|---|
| 2014/0206845 A1 | 7/2014 | Kameoka et al. |
| 2015/0197564 A1 | 7/2015 | Sleeman et al. |
| 2016/0115246 A1 | 4/2016 | Sasiela et al. |
| 2017/0037124 A1 | 2/2017 | Gusarova et al. |
| 2017/0037409 A1 | 2/2017 | Freier et al. |
| 2017/0233466 A1 | 8/2017 | Gromada |
| 2017/0253666 A1 | 9/2017 | Gusarova |
| 2017/0291937 A1 | 10/2017 | Gromada |
| 2017/0312359 A1 | 11/2017 | Pordy |
| 2019/0092845 A1 | 3/2019 | Sleeman et al. |
| 2019/0315851 A1 | 10/2019 | Sleeman et al. |
| 2020/0061189 A1 | 2/2020 | Pordy |
| 2020/0079841 A1 | 3/2020 | Gromada |
| 2020/0369760 A1 | 11/2020 | Liu |
| 2020/0377583 A1 | 12/2020 | Gromada |
| 2022/0072127 A1 | 3/2022 | Pordy |
| 2022/0089711 A1 | 3/2022 | Gromada |
| 2022/0127348 A1 | 4/2022 | Gromada |
| 2022/0153825 A1 | 5/2022 | Sleeman |
| 2022/0403016 A1 | 12/2022 | Sleeman |
| 2023/0000976 A1 | 1/2023 | Pordy |

FOREIGN PATENT DOCUMENTS

| | | |
|---|---|---|
| CN | 109069868 A | 12/2018 |
| EP | 1482041 | 12/2004 |
| EP | 2735315 | 5/2014 |
| JP | 2002-521475 | 7/2002 |
| JP | 2002-536459 | 10/2002 |
| JP | 2005080508 | 3/2005 |
| JP | 2010-512320 | 4/2010 |
| JP | 2012-511913 | 5/2012 |
| JP | 2012-518639 | 8/2012 |
| JP | 2015-536934 | 12/2015 |
| TW | 200846364 | 12/2008 |
| WO | 2003/044172 | 5/2003 |
| WO | 2006/098887 | 9/2006 |
| WO | 2008/073300 | 6/2008 |
| WO | 2009/100318 | 8/2009 |
| WO | 2010/111892 | 10/2010 |
| WO | 2011/008773 | 1/2011 |
| WO | 2011/085271 | 7/2011 |
| WO | 2012/174178 | 12/2012 |
| WO | 2014-066468 | 5/2014 |
| WO | 2014/152776 | 9/2014 |
| WO | 2014/194168 | 12/2014 |
| WO | 2015/077154 | 5/2015 |
| WO | 2015/100394 | 7/2015 |
| WO | 2016/011256 | 1/2016 |
| WO | 2016/054494 | 4/2016 |
| WO | 2017027316 | 2/2017 |
| WO | 2017177181 | 12/2017 |
| WO | 2018/187057 | 10/2018 |

OTHER PUBLICATIONS

Kotla, S. et al., "The Transcription Factor CREB Enhances Interleukin-17A Production and Inflammation in a Mouse Model of Atherosclerosis", Science Signaling, Sep. 17, 2013, vol. 6, No. 293, ra83, pp. 1-13.
Zhang, Bao-yu et al., "The correlation study on angiopoietin-like protein 3 and diabetic angiopathies, dyslipidemia", English abstract, Proceedings of Clinical Medicine, vol. 23, No. 8, Aug. 31, 2014, pp. 565-568.
Ando et al., (2003) J. Lipid. Res 44(6):1216-1223, "A decreased expression of angiopoietin-like 3 is protective against atherosclerosis in apoE-deficient mice".
Borodovsky et al., (2014) Alnylam Pharmaceuticals, "Developments of Monthly to Quarterly Subcutaneous Administration of RNAi Therapeutics Targeting the Metabolic Disease Genes PCSK9, ApoC3 and ANGPTL3 ALN-PCS Phase I Study Results" Website [Online] Available Website: www.alnylam.com/web/assets/ Cardiometaboliclike_AHA_Poster_111714.pdf; Last Update: unknown; Accessed on: May 9, 2017.
Camenisch et al., (2002) J. Biol. Chem. 277(19):17281-17290, "ANGPTL3 Stimulates Endothelial Cell Adhesion and Migration via Integrin alpha v beta 3 and induces Blood Vessel Formation in Vivo".
Conklin et al. (1999) Genomics 62(3):477-482, "Identification of a Mammalian Angiopoietin-Related Protein Expressed Specifically in Liver".
Correia (2010) mAbs 2(3):221-232, "Stability of IgG isotypes in serum".
Ecuadorian English translation of the opposition brief dated Mar. 13, 2015 for corresponding Ecuadorian application No. SP 2013-13085.
Gaudet (2016) Journal of Clinical Lipidology 10(3):715 "Safety and Efficacy of Evinacumab, a monoclonal antibody to ANGPTL3, in Patients with Homozygous Familial Hypercholesterolemia Receiving Concomitant Lipid-Lowering Therapies".
Gaudet (2017) Journal of Clinical Lipidology 11(3): 837-838 "Safety and Efficacy of Evinacumab, A Monoclonal Antibody to ANGPTL3, in Homozygous Familial Hypercholesterolemia".
Gusarova, "ANGPTL3 Blockage with a Human Monoclonal Antibody Reduces Plasma Lipids in Dyslipidemic Mice and Monkeys", (2015), Journal of Lipid Research 56(7):1308-1317.
Koishi et al., (2002) Nat. Genet. 30(2):151-157, "Angptl3 regulates lipid metabolism in mice".
Kuhnast et al. (2014) J Lipid Res. 55(10):2103-2112 "Alirocumab inhibits atherosclerosis, improves the plaque morphology, and enhances the effects of a statin".
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)", Journal of Biological Chemistry (2009), 284(20), 13735-13745.
Ono, Mitsuru et al., "Protein Region Important for Regulation of Lipid Metabolism in Angiopoietin-like 3 (ANGTPL3): ANGPTL3 Is Cleaved and Activated In Vivo", Oct. 24, 2003, Journal of Biological Chemistry, The American Society of Biological Chemists, Inc. 278(43):41804-41809.
Rader et al. (2015) Cell Metabolism 23(3): 405-412 "New Therapeutic Approaches to the Treatment of Dyslipidemia".
Rossetti and Goldberg (2002) Nat. Med. 8(2):112-114, "A new piece in the diabetes puzzle".
Shimamura et al., "Leptin and insulin down-regulate angiopoietin-like protein 3, a plasma triglyceride-increasing factor", Biochemical and Biophysical Research Communications (2004), 322(3), 1080-1085.
Shimizugawa et al., (2002) J. Biol. Chem. 277(37):33742-33748, "ANGPTL3 Decreases Very Low Density Lipoprotein Triglyceride Clearance by Inhibition of Lipoprotein Lipase".
Sonnenburg et al. GPIHBP1 stabilizes lipoprotein lipase and prevents its inhibition by angiopoietin-like 3 and angiopoietin-like 4. Journal of Lipid Research (2009), 50(12), 2421-2429.
Tikka et al. (2016) Endocrine 52(2):187-193 "The Role of ANGPTL3 in Controlling Lipoprotein Metabolism".
Wang (2015) Journal of Lipid Research 56(7):1296-1307 "Inactivation of ANGPTL3 Reduces Hepatic VLDL-Triglyceride Secretion".
Yau et al., "A Highly Conserved Motif within the NH2-terminal Coiled-coil Domain of Angiopoietin-like Protein 4 Confers Its Inhibitory Effects on Lipoprotein Lipase by Disrupting the Enzyme Dimerization", Journal of Biological Chemistry (2009), 284(18),1942-11952.
Yeadon, J., "Which Jax Mouse Model is Best for Atherosclerosis Studies: Apoe or LDLR Knockout Mice?", The Jackson Laboratory, https://www.jax.org/news-and-insights/jax-blog/2013/november/which-jax-mouse-model-is-best-for-atherosclerosis-studies-apoe-or-ldlr-knoc, 1 page, 2018.
Brandt, Teresa, et al., "ISIS-ANGPTL3RX, an antisense inhibitor to angiopoietin-like 3, reduces plasma lipid levels in mouse models and in healthy human volunteers", Abstracts EAS-0824/ Atherosclerosis 241 (Jul. 2015) e1-e31.
Calandra et al., "Familial combined hypolipidemia due to mutations in the ANGPTL3 gene", Clinical Lipidology, 2013, 8: 1, 81-95.

(56) References Cited

OTHER PUBLICATIONS

Fenzl et al., "Circulating betatrophin correlates with atherogenic lipid profiles but not with glucose and insulin levels in insulin-resistant individuals", Diabetologia (2014), 57(6), 1204-1208.
Huijgen et al., "Genetic variation in APOB, PCSK9, and ANGPTL3 in carriers of pathogenic autosomal dominant hypercholesterolemic mutations with unexpected low LDL-C levels", Human Mutation 2012;33(2):448-455, 19 pages.
Liakos et al., "PCSK9—targeting monoclonal antibodies for the management of hypercholesterolemia: a systematic review and meta—analysis", Jun. 1, 2014, online at: http://www.crd.york.ac.uk/PROSPEROFILES/7051_PROTOCOL_20140008.pdf, 16 pages.
Musunuru et al., "Exome Sequencing, ANGPTL3 Mutations, and Familial Combined Hypolipidemia", The New England Journal of Medicine, 363;23:2220-2227, Dec. 2, 2010.
O'Riordan, Mike, "Gene Mutations Linked With Low LDL-Cholesterol Levels: ANGPTL3. ANGPTL3 and LDL Cholesterol", Oct. 15, 2010, pp. 1-2, located online at: https://www.medscape.com/viewarticle/730654.
Pramfalk et al., "Effects of high-dose statin on the human hepatic expression of genes involved in carbohydrate and triglyceride metabolism", J Intern Med 2011;269: 333-339.
Turner et al., "Non-statin Treatments for Managing LDL Cholesterol and Their Outcomes", Clinical Therapeutics/ vol. 37, No. 12:2751-2769, Dec. 1, 2015.
Oike, Y. et al., "Angiopoietin-like proteins: potential new targets for metabolic syndrome therapy", Trends in Molecular Medicine, Oct. 2005, vol. 11, No. 10, pp. 473-479.
Montero-Julian, Felix A. et al., "Pharmacokinetic Study of Anti-Interleukin-6 (IL-6) Therapy With Monoclonal Antibodies: Enhancement of IL-6 Clearance by Cocktails of Anti-IL-6 Antibodies", Blood, vol. 85, No. 4, Feb. 15, 1995, pp. 917-924.
Broxmeyer, H.E. et al., "Angiopoietin-like-2 and -3 act through their coiled-coil domains to enhance survival and replating capacity of human cord blood hematopoietic progenitors", Blood Cells, Molecules, and Diseases 48 (2012), Oct. 7, 2011, pp. 25-29, abstract.
Labrijn, Aran F. et al., "Therapeutic lgG4 antibodies engage in Fab-arm exchange with endogenous human lgG4 in vivo", Nature Biotechnology, (Aug. 2009), vol. 27, No. 8, pp. 767-771.
Karlsson, Robert, et al., "Affinity Measurement Using Surface Plasmon Resonance", Methods in Molecular Biology, (2004), vol. 248, pp. 389-415.
Haller, Jorge F., et al., "ANGPTL8 requires ANGPTL3 to inhibit lipoprotein lipase and plasma triglyceride clearance," Journal of Lipid Research, vol. 58, No. 6, Jun. 1, 2017, pp. 1166-1173, XP55387875.
Hanson, Robert L. et al., "The ARG59Trp Variant in ANGPTL8 (betatrophin) is Associated with Total and HDL-Cholesterol in American Indians and Mexican Americans and Differentially Affects Cleavage of ANGPTL3", Molecular Genetics and Metabolism Academic Press, Amsterdam, NL, 118(2):128-137.
Zhang, Ren, "The ANGPTL3-4-8 model, a molecular mechanism for triglyceride trafficking," Open Biology, vol. 6, No. 4, Apr. 1, 2016, p. 150727, XP55387866.
Lloyd et al., "Modelling the human immune response: performance of a $10^{11}$ human antibody repertoire against a broad panel of therapeutically relevant antigens", Protein Engineering, Design & Selection vol. 22, No. 3, 2009, pp. 159-168.
Ito, Matthew K et al., "Challenges in the Diagnosis and Treatment of Homozygous Familial Hypercholesterolemia.", Drugs vol. 75, 15, 2015: 1715-24. doi:10.1007/s40265-015-0466-y (abstract, Table 1).
Nachtigal P et al., "Atorvastatin has hypolipidemic and anti-inflammatory effects in apoE/LDL receptor-double-knockout mice", Life Sci. Mar. 26, 2008; 82 (13-14):708-17.) doi: 10.1016/j.lfs.2008.01.006. Epub Jan. 26, 2008. PMID: 18289605 (abstract).
Quagliarini, Fabina et al., "Atypical angiopoietin-like protein that regulates ANGPTL3", Proc Natl Acad Sci USA, Nov. 27, 2012, pp. 19751-19756.

Ahn, Chang Ho, et al., "New Drugs for Treating Dyslipidemia: Beyond Statins", Diabetes & Metabolism Journal, vol. 39, No. 2, Apr. 20, 2015, pp. 87-94.
Wang, Yan, et al., "Mice lacking ANGPTL8 (Betatrophin) manifest disrupted triglyceride metabolism without impaired glucose homeostasis", PNAS, Oct. 1, 2013, vol. 10, No. 40, pp. 16109-16114.
Myers, Calisha, "Aegerion Pharmaceuticals, Inc. Announces AEGR-733 Phase II Data Demonstrates Significant Lowering of LD Cholesterol, Nov. 6, 2008, online at https://www.fiercebiotech.com/biotech/aegerion-pharmaceuticals-inc-announces-aegr-733-phase-ii-data-demonstrates-significant", 5 pgs.
Lyudmila Georgieva Vladimiriova-Kitova et al., "Resistance of Statin Therapy, and Methods for its Influence", In: "Hypercholesterolemia", Sep. 17, 2015, InTech, Chapter 10, 19 pages.
Farnier, M. et al., "Efficacy of alirocumab in heterozygous familial hypercholesterolemia or high cv risk populations: pooled analyses of eight phase 3 trials", Abstracts, EAS-0563, Atherosclerosis, vol. 241, No. 1, 2015, 2 pages.
Carpenter, J.F. et al., "Rational Design of Stable Lyophilized Protein Formulations: Some Practical Advice", Pharmaceutical Research, vol. 14, No. 8, Jan. 1, 1997, pp. 969-975.
Wang, Wei Ed—Blanco-Prieto, Maria et al., "Instability, stabilization, and formulation of liquid protein pharmaceuticals", vol. 185, No. 2, Aug. 20, 1999, pp. 129-188.
Banerjee, Poulabi et al., "Functional Analysis of LDLR (Low-Density Lipoprotein Receptor) Variants in Patient Lymphocytes to Assess the Effect of Evinacumab in Homozygous Familial Hypercholesterolemia Patients With a Spectrum of LDLR Activity", Translational Sciences, vol. 39, No. 11, Nov. 1, 2019, pp. 2248-2260.
Rosenson, Robert S. et al., "Evinacumab in Patients with Refractory Hypercholesterolemia", The New England Journal of Medicine,vol. 383, No. 24, Dec. 10, 2020, pp. 2307-2319.
Raal, Frederick J., et al., "Evinacumab for Homozygous Familial Hypercholesterolemia", The New England Journal of Medicine,vol. 383, No. 8, Aug. 20, 2020, pp. 711-720.
Sirtori et al., "Microsomal transfer protein (MTP) inhibition—a novel approach to the treatment of homozygous hypercholesterolemia", Annals of Medicine, 46:7, 464-474, 2014.
Cuchel et al., Abstract 1077: A Phase III Study of Microsomal Triglyceride Transfer Protein Inhibitor Lomitapide (AEGR-733) in Patients With Homozygous Familial Hypercholesterolemia: Interim Results at 6 Months, Circulation, 2009, 120: S441.
DeGoma, E.M., "Lomitapide for the Management of Homozygous Familial Hypercholesterolemia", Rev. Cardiovasc Med., 2014;15(2), 109-118.
Wardemann, Hedda et al., "Predominant Autoantibody Production by Early Human B Cell Precursors", Science 301, 1374-1377 (2003).
Singer, Maxine et al., "Genes and Genomes", in 2 volumes, Moscow, Mir, 1998, vol. 1, pp. 64, 67 (translated pages correspond to cited pages).
Masana, Luis et al., "Unmet Needs: Patients with Statin Intolerance or Familial Hypercholesterolemia", Clin Investig Arterioscler, May 28, 2016, Suppl 2:22-30, English abstract.
Bitzur, Rafael et al., "Intolerance to Statins: Mechanisms and Management", Diabetes Care, vol. 36, Supp. 2, Aug. 2013, S325-S330.
Arca, Marcello et al., "Treating statin-intolerant patients", Diabetes, Metabolic Syndrome and Obesity: Targets and Therapy, Dove Press, Apr. 27, 2011, pp. 155-166.
Mayo Clinic, "Niacin", dated Nov. 12, 2020, located online at: https://www.mayoclinic.org/drugs-supplements-niacin/art-20364984#:~:text=Prescription%20niacin%20might%20benefit%20people%20with%20high%20cholesterol,in%20appropriate%20amounts%2C%20niacin%20appears%20to%20be%20safe, 4 pages.
Mayo Clinic, "Niacin to improve cholesterol numbers", Jun. 7, 2022, located online at: https://www.mayoclinic.org/diseases-conditions/high-blood-cholesterol/in-depth/niacin/art-20046208, 3 pages.
Kang, Jichao et al., "Rapid Formulation Development for Monoclonal Antibodies", published Apr. 12, 2016, obtained online at

(56) References Cited

OTHER PUBLICATIONS

BioProcess International on Jan. 30, 2023 at: http://www.bioprocessintl.com/manufacturing/formulation/rapid-formulation-development-for-monoclonal-antibodies/, 7 pages.
Wang, Wei, et al., "Antibody structure, instability, and formulation", J Pharm Sci. Jan. 2007;96(1): 1-26.
Fu, Zhiyao et al., "A Lipasin/ANGPTL8 Monoclonal Antibody Lowers Mouse Serum Triglycerides Involving Increased Postprandial Activity of the Cardiac Lipoprotein C6 Lipase", (Dec. 21, 2015) Scientific Reports 5(1):5.
Hartgers, Merel et al., "New Approaches in Detection and Treatment of Familial Hypercholesterolemia", Curr Cardiol Rep (2015) 17: 109, 8 pages.
Hung, Jessica et al., "Improving Viscosity and Stability of a Highly Concentrated Monoclonal Antibody Solution with Concentrated Proline", Pharm Res (2018) 35: 133, 14 pages; https://doi.org/10.1007s/11095-018-2398-1.
Rosenson, Robert S. et al., "Evinacumab in severe hypertriglyceridemia with or without lipoprotein lipase pathway mutations: a phase 2 randomized trial", Nature Medicine, vol. 29, Mar. 2023; 729-737.
Goldberg, Ronald et al., "A Comprehensive Update on the Chylomicronemia Syndrome", Frontiers in Endocrinology, Oct. 23, 2020, vol. 11, article 593931, 13 pages.
Gidding, Sam et al., "The Agenda for Familial Hypercholesterolemia: A Scientific Statement From the American Heart Association", Circulation, 2015; 132:2167-2192; downloaded from http://ahajournals.org on Dec. 15, 2023.
Oldoni et al., "ANGPTL8 has both endocrine and autocrine effects on substrate utilization", JCI Insight 2020; 5(17): e138777, 19 pages.
Rosenson, Robert et al., "Abstract 12054: Evinacumab Reduces Atherogenic Lipids and Apolipoprotein B in Patients with Severe Hypertriglyceridemia", Circulation, vol. 144, No. Suppl_1, Nov. 8, 2021, 2 pages.
Rosenson, Robert et al., P742/#696, E-Posters Topic, "A Phase 2 trial of the efficacy and safety of evinacumab in patients with severe hypertriglyceridemia" Atherosclerosis, Elsevier, vol. 331,Aug. 1, 2021, p. e293.
Shamsudeen, Isabel et al., "Safety and efficacy of therapies for chylomicronemia", Expert Review of Clinical Pharmacology 20141101 Expert Reviews Ltd, GBR, vol. 15, No. 4, Apr. 3, 2022, 12 pages.
Immunology Illustrated, 5th Edition, pp. 71-82, Nankodo Corporation, 2000,(Original: Immunology Fifth Edition by Ivan Roitt, Jonathan Brostoff and David Male), with partial English translation, 23 pages with translation.
Kolansky et al., "Longitudinal Evaluation and Assessment of Cardiovascular Disease in Patients with Homozygous Familial Hypercholesterolemia", 2008, The American Journal of Cardiology 102:1438-1443.
Santos et al., "Type of LDLR mutation and the pharmacogenetics of familial hypercholesterolemia treatment", 2015 Pharmacogenomics 16:1743-1750.
Rader, Daniel J. et al., "Lomitapide and Mipomersen: Two First-in-Class Drugs for Reducing Low-Density Lipoprotein Cholesterol in Patients with Homozygous Familial Hypercholesterolemia", 2014 Circulation 129, Issue 9:1022-1032.

SEQUENCE LISTING

```
<160> NUMBER OF SEQ ID NOS: 23

<210> SEQ ID NO 1
<211> LENGTH: 460
<212> TYPE: PRT
<213> ORGANISM: Artificial Sequence
<220> FEATURE:
<223> OTHER INFORMATION: hANGPTL3

<400> SEQUENCE: 1

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160
```

```
Val Thr Ser Leu Lys Thr Phe Val Glu Lys Gln Asp Asn Ser Ile Lys
            165                 170                 175

Asp Leu Leu Gln Thr Val Glu Asp Gln Tyr Lys Gln Leu Asn Gln Gln
        180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
        290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 2
<211> LENGTH: 126
<212> TYPE: PRT
<213> ORGANISM: Artificial Sequence
<220> FEATURE:
<223> OTHER INFORMATION: HCVR

<400> SEQUENCE: 2

Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Gly Pro Gly Lys Gly Leu Glu Trp Val
        35                  40                  45

Ser Ala Ile Ser Gly Asp Gly Gly Ser Thr Tyr Tyr Ala Asp Ser Val
    50                  55                  60
```

```
Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Phe Phe Tyr Cys
                 85                  90                  95

Ala Lys Asp Leu Arg Asn Thr Ile Phe Gly Val Val Ile Pro Asp Ala
            100                 105                 110

Phe Asp Ile Trp Gly Gln Gly Thr Met Val Thr Val Ser Ser
        115                 120                 125
```

```
<210> SEQ ID NO 3
<211> LENGTH: 108
<212> TYPE: PRT
<213> ORGANISM: Artificial Sequence
<220> FEATURE:
<223> OTHER INFORMATION: LCVR

<400> SEQUENCE: 3
```

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Arg Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Tyr
                 85                  90                  95

Thr Phe Gly Gln Gly Thr Lys Leu Glu Ile Lys Arg
            100                 105
```

```
<210> SEQ ID NO 4
<211> LENGTH: 8
<212> TYPE: PRT
<213> ORGANISM: Artificial Sequence
<220> FEATURE:
<223> OTHER INFORMATION: HCDR1

<400> SEQUENCE: 4
```

```
Gly Phe Thr Phe Asp Asp Tyr Ala
 1               5
```

```
<210> SEQ ID NO 5
<211> LENGTH: 8
<212> TYPE: PRT
<213> ORGANISM: Artificial Sequence
<220> FEATURE:
<223> OTHER INFORMATION: HCDR2

<400> SEQUENCE: 5
```

```
Ile Ser Gly Asp Gly Gly Ser Thr
 1               5
```

```
<210> SEQ ID NO 6
<211> LENGTH: 19
<212> TYPE: PRT
<213> ORGANISM: Artificial Sequence
<220> FEATURE:
<223> OTHER INFORMATION: HCDR3

<400> SEQUENCE: 6
```

Ala Lys Asp Leu Arg Asn Thr Ile Phe Gly Val Val Ile Pro Asp Ala
1               5                   10                  15

Phe Asp Ile

<210> SEQ ID NO 7
<211> LENGTH: 6
<212> TYPE: PRT
<213> ORGANISM: Artificial Sequence
<220> FEATURE:
<223> OTHER INFORMATION: LCDR1

<400> SEQUENCE: 7

Gln Ser Ile Arg Ser Trp
1               5

<210> SEQ ID NO 8
<211> LENGTH: 3
<212> TYPE: PRT
<213> ORGANISM: Artificial Sequence
<220> FEATURE:
<223> OTHER INFORMATION: LCDR2

<400> SEQUENCE: 8

Lys Ala Ser
1

<210> SEQ ID NO 9
<211> LENGTH: 9
<212> TYPE: PRT
<213> ORGANISM: Artificial Sequence
<220> FEATURE:
<223> OTHER INFORMATION: LCDR3

<400> SEQUENCE: 9

Gln Gln Tyr Asn Ser Tyr Ser Tyr Thr
1               5

<210> SEQ ID NO 10
<211> LENGTH: 453
<212> TYPE: PRT
<213> ORGANISM: Artificial Sequence
<220> FEATURE:
<223> OTHER INFORMATION: HC

<400> SEQUENCE: 10

Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Gly Pro Gly Lys Gly Leu Glu Trp Val
        35                  40                  45

Ser Ala Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Phe Phe Tyr Cys
                85                  90                  95

Ala Lys Asp Leu Arg Asn Thr Ile Phe Gly Val Val Ile Pro Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr

```
            130                 135                 140
Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 11
<211> LENGTH: 214
<212> TYPE: PRT
<213> ORGANISM: Artificial Sequence
<220> FEATURE:
<223> OTHER INFORMATION: LC

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
```

```
                35                  40                  45
Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 118
<212> TYPE: PRT
<213> ORGANISM: Artificial Sequence
<220> FEATURE:
<223> OTHER INFORMATION: alirocumab HCVR

<400> SEQUENCE: 12

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 13
<211> LENGTH: 8
<212> TYPE: PRT
<213> ORGANISM: Artificial Sequence
<220> FEATURE:
<223> OTHER INFORMATION: alirocumab HCDR1

<400> SEQUENCE: 13
```

```
Gly Phe Thr Phe Asn Asn Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: alirocumab HCDR2

<400> SEQUENCE: 14

Ile Ser Gly Ser Gly Gly Thr Thr
1               5

<210> SEQ ID NO 15
<211> LENGTH: 11
<212> TYPE: PRT
<213> ORGANISM: Artificial Sequence
<220> FEATURE:
<223> OTHER INFORMATION: alirocumab HCDR3

<400> SEQUENCE: 15

Ala Lys Asp Ser Asn Trp Gly Asn Phe Asp Leu
1               5                   10

<210> SEQ ID NO 16
<211> LENGTH: 447
<212> TYPE: PRT
<213> ORGANISM: Artificial Sequence
<220> FEATURE:
<223> OTHER INFORMATION: alirocumab HC

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
                210                 215                 220
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 17
<211> LENGTH: 113
<212> TYPE: PRT
<213> ORGANISM: Artificial Sequence
<220> FEATURE:
<223> OTHER INFORMATION: alirocumab LCVR

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 18
```

```
<211> LENGTH: 12
<212> TYPE: PRT
<213> ORGANISM: Artificial Sequence
<220> FEATURE:
<223> OTHER INFORMATION: alirocumab LCDR1

<400> SEQUENCE: 18

Gln Ser Val Leu Tyr Arg Ser Asn Asn Arg Asn Phe
1               5                   10

<210> SEQ ID NO 19
<211> LENGTH: 3
<212> TYPE: PRT
<213> ORGANISM: Artificial Sequence
<220> FEATURE:
<223> OTHER INFORMATION: alirocumab LCDR2

<400> SEQUENCE: 19

Trp Ala Ser
1

<210> SEQ ID NO 20
<211> LENGTH: 220
<212> TYPE: PRT
<213> ORGANISM: Artificial Sequence
<220> FEATURE:
<223> OTHER INFORMATION: alirocumab LC

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
                20                  25                  30

Ser Asn Asn Arg Asn Phe Leu Gly Trp Tyr Gln Gln Lys Pro Gly Gln
            35                  40                  45

Pro Pro Asn Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 21
<211> LENGTH: 9
```

```
<212> TYPE: PRT
<213> ORGANISM: Artificial Sequence
<220> FEATURE:
<223> OTHER INFORMATION: alirocumab LCDR3

<400> SEQUENCE: 21

Gln Gln Tyr Tyr Thr Thr Pro Tyr Thr
1               5

<210> SEQ ID NO 22
<211> LENGTH: 2076
<212> TYPE: DNA
<213> ORGANISM: Artificial Sequence
<220> FEATURE:
<223> OTHER INFORMATION: hPCSK9

<400> SEQUENCE: 22
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc cgaggaggac ggcctggccg aagcacccga gcacggaacc   180
acagccacct ccaccgctg cgccaaggat ccgtggaggt tgcctggcac ctacgtggtg   240
gtgctgaagg aggagaccca cctctcgcag tcagagcgca ctgcccgccg cctgcaggcc   300
caggctgccc gccggggata cctcaccaag atcctgcatg tcttccatgg ccttcttcct   360
ggcttcctgg tgaagatgag tggcgacctg ctggagctgg ccttgaagtt gccccatgtc   420
gactacatcg aggaggactc ctctgtcttt gcccagagca tcccgtggaa cctggagcgg   480 attcccctc acggtaccg ggcggatgaa taccagcccc ccgacggagg cagcctggtg   540
gaggtgtatc tcctagacac cagcatacag agtgaccacc gggaaatcga gggcagggtc   600
atggtcaccg acttcgagaa tgtgcccgag gaggacggga cccgcttcca cagacaggcc   660
agcaagtgtg acagtcatgg cacccacctg gcagggtgg tcagcggccg ggatgccggc   720
gtggccaagg tgccagcat gcgcagcctg cgcgtgctca actgccaagg aagggcacg   780 gttagcggca ccctcatagg cctggagttt attcggaaaa gccagctggt ccagcctgtg   840
gggccactgg tggtgctgct gccccctggc ggtgggtaca gccgcgtcct caacgccgcc   900
tgccagcgcc tggcgagggc tggggtcgtg ctggtcaccg ctgccggcaa cttccgggac   960
gatgcctgcc tctactcccc agcctcagct cccgaggtca tcacagttgg ggccaccaat  1020
gcccaagacc agccggtgac cctggggact ttggggacca ctttggccg ctgtgtggac  1080 ctctttgccc caggggagga catcattggt gcctccagcg actgcagcac ctgctttgtg  1140
tcacagagtg ggacatcaca ggctgctgcc cacgtggctg gcattgcagc catgatgctg  1200
tctgccgagc cggagctcac cctggccgag ttgaggcaga gactgatcca cttctctgcc  1260
aaagatgtca tcaatgaggc ctggttccct gaggaccagc gggtactgac ccccaacctg  1320
gtggccgccc tgccccccag cacccatggg caggttggc agctgttttg caggactgta  1380
tggtcagcac actcggggcc tacacggatg ccacagccg tcgcccgctg cgccccagat  1440
gaggagctgc tgagctgctc cagtttctcc aggagtggga gcggcgggg cgagcgcatg  1500 gaggcccaag ggggcaagct ggtctgccgg gcccacaacg cttttggggg tgagggtgtc  1560
tacgccattg ccaggtgctg cctgctaccc caggccaact gcagcgtcca cacagctcca  1620
ccagctgagg ccagcatggg gacccgtgtc cactgccacc aacagggcca cgtcctcaca  1680
ggctgcagct cccactggga ggtggaggac cttggcaccc acaagccgcc tgtgctgagg  1740
ccacgaggtc agcccaacca gtgcgtgggc cacagggagg ccagcatcca cgcttcctgc  1800
```

```
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctggggc ctacgccgta gacaacacgt gtgtagtcag gagccgggac    1980
gtcagcacta caggcagcac cagcgaaggg gccgtgacga ccgttgccat ctgctgccgg    2040
agccggcacc tggcgcaggc ctcccaggag ctccag                              2076
```

<210> SEQ ID NO 23
<211> LENGTH: 692
<212> TYPE: PRT
<213> ORGANISM: Artificial Sequence
<220> FEATURE:
<223> OTHER INFORMATION: hPCSK9

<400> SEQUENCE: 23

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
```

```
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
                340                 345                 350
Thr Asn Phe Gly Arg Cys Val Asp Leu Phe Ala Pro Gly Glu Asp Ile
                355                 360                 365
Ile Gly Ala Ser Ser Asp Cys Ser Thr Cys Phe Val Ser Gln Ser Gly
                370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
Gln Arg Val Leu Thr Pro Asn Leu Val Ala Ala Leu Pro Pro Ser Thr
                435                 440                 445
His Gly Ala Gly Trp Gln Leu Phe Cys Arg Thr Val Trp Ser Ala His
                450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
                515                 520                 525
Leu Pro Gln Ala Asn Cys Ser Val His Thr Ala Pro Pro Ala Glu Ala
                530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
                580                 585                 590
Glu Ala Ser Ile His Ala Ser Cys Cys His Ala Pro Gly Leu Glu Cys
                595                 600                 605
Lys Val Lys Glu His Gly Ile Pro Ala Pro Gln Glu Gln Val Thr Val
                610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
                660                 665                 670
Thr Ala Val Ala Ile Cys Cys Arg Ser Arg His Leu Ala Gln Ala Ser
                675                 680                 685
Gln Glu Leu Gln
690
```

METHODS FOR TREATING PATIENTS WITH HYPERLIPIDEMIA BY ADMINISTERING A PCSK9 INHIBITOR IN COMBINATION WITH AN ANGPTL3 INHIBITOR

CROSS-REFERENCE TO RELATED APPLICATIONS

This application is a continuation of application Ser. No. 15/446,720, filed on Mar. 1, 2017, which claims the benefit under 35 U.S.C. § 119(e) of U.S. provisional application No. 62/302,907, filed on Mar. 3, 2016. The disclosure of the aforementioned patent applications are herein incorporated by reference in their entirety.

FIELD OF THE INVENTION

The present invention relates to the field of therapeutic treatments of diseases and disorders, which are associated with elevated levels of lipids and lipoproteins. More specifically, the invention relates to the use of a proprotein convertase subtilisin/kexin type 9 (PCSK9) inhibitor in combination with an inhibitor of angiopoietin-like protein 3 (ANGPTL3) to treat patients with hypercholesterolemia and related conditions, who are non-responsive to, inadequately controlled by, or intolerant to treatment with a standard lipid modifying therapy.

BACKGROUND

Hyperlipidemia is a general term that encompasses diseases and disorders characterized by or associated with elevated levels of lipids and/or lipoproteins in the blood. Hyperlipidemias include hypercholesterolemia, hypertriglyceridemia, combined hyperlipidemia, and elevated lipoprotein a (Lp(a)). A particular prevalent form of hyperlipidemia in many populations is hypercholesterolemia.

Hypercholesterolemia, particularly an increase in low-density lipoprotein (LDL) cholesterol (LDL-C) levels, constitutes a major risk for the development of atherosclerosis and coronary heart disease (CHD) (Sharrett et al., 2001, Circulation 104:1108-1113). Low-density lipoprotein cholesterol is identified as the primary target of cholesterol lowering therapy and is accepted as a valid surrogate therapeutic endpoint. Numerous studies have demonstrated that reducing LDL-C levels reduces the risk of CHD with a strong direct relationship between LDL-C levels and CHD events; for each 1 mmol/L (~40 mg/dL) reduction in LDL-C, cardiovascular disease (CVD) mortality and morbidity is lowered by 22%. Greater reductions in LDL-C produce greater reduction in events, and comparative data of intensive versus standard statin treatment suggest that the lower the LDL-C level, the greater the benefit in patients at very high cardiovascular (CV) risk.

Familial hypercholesterolemia (FH) is an inherited disorder of lipid metabolism that predisposes a person to premature severe cardiovascular disease (CVD) (Kolansky et al., (2008), Am J Cardiology, 102(11):1438-1443). FH can be either an autosomal dominant or an autosomal recessive disease that results from mutations in the low density lipoprotein receptor (LDLR), or in at least 3 different genes that code for proteins involved in hepatic clearance of LDL-C can cause FH. Examples of such defects include mutations in the gene coding for the LDL receptor (LDLR) that removes LDL-C from the circulation, and in the gene for apolipoprotein (Apo) B, which is the major protein of the LDL particle. In certain cases of FH, the gene coding for proprotein convertase subtilisin/kexin type 9 (PCSK9), an enzyme involved in degrading the LDLR (gain of function mutation), is mutated. In all cases, FH is characterized by an accumulation of LDL-C in the plasma from birth and subsequent development of tendon xanthomas, xanthelasmas, atheromata, and CVD. FH can be classified as either heterozygous FH (heFH) or homozygous FH (hoFH) depending on whether the individual has a genetic defect in one (heterozygous) or both (homozygous) copies of the implicated gene.

Current LDL-C-lowering medications include statins, cholesterol absorption inhibitors, fibrates, niacin, and bile acid sequestrants. Statins are a commonly prescribed treatment for LDL-C lowering. However, despite the availability of such lipid-lowering therapies, many high-risk patients fail to reach their guideline target LDL-C level (Gitt et al., 2010, Clin Res Cardiol 99(11):723-733). For patients who are still unable to achieve guideline target level for LDL-C, despite available lipid-modifying therapy (LMT), mechanical removal of LDL-C by lipoprotein apheresis (e.g., LDL apheresis) is sometimes prescribed.

However, patients who are not at LDL-C goal despite receiving an optimized LMT regiment, would greatly benefit from alternative LDL-C lowering therapies, or through use of a combination of therapeutic agents, such as the agents and regimens described herein.

BRIEF SUMMARY OF THE INVENTION

The present invention provides methods for treating hyperlipidemia in patients who are non-responsive to, inadequately controlled by, or intolerant to treatment with a standard lipid modifying therapy. The therapeutic methods of the present invention result in a lowering of serum lipoprotein levels to a normal and acceptable range and as such, may act to reduce the risk of development of atherosclerosis, or coronary heart disease.

In one aspect, the invention provides a method of treating a patient suffering from hypercholesterolemia, wherein the patient is non-responsive to, inadequately controlled by, or intolerant to treatment with a standard lipid modifying therapy, the method comprising treating the patient with a combination of a proprotein convertase subtilisin/kexin type 9 (PCSK9) inhibitor and an inhibitor of angiopoietin-like protein 3 (ANGPTL3).

In one embodiment, the invention provides administering one or more doses of a PCSK9 inhibitor in combination with one or more doses of an ANGPTL3 inhibitor to a patient who is being treated, or has been treated with a standard lipid modifying therapy, but has not responded to such therapy. Administration of a combination of a PCSK9 inhibitor with an ANGPTL3 inhibitor to the patient results in lowering the level of at least one lipoprotein in the serum of the patient and consequently reduces or eliminates the need for treatment with the standard lipid lowering therapy by the patient.

In a related aspect, the methods of the present invention comprise selecting a patient with hypercholesterolemia who is being treated, or has been treated with a standard lipid lowering therapy and who is non-responsive to, inadequately controlled by, or intolerant to, such therapy and administering one or more doses of a PCSK9 antibody in combination with one or more doses of an ANGPTL3 antibody to the patient, thereby lowering the level of at least one lipoprotein in the serum of the patient and consequently replacing the use of the standard lipid modifying therapy with the combination therapy of a PCSK9 antibody plus an ANGPTL3 antibody to achieve a target lipoprotein level.

Patients who are treated or treatable by the methods of the present invention include, e.g., patients with hypercholesterolemia, including patients with familial hypercholesterolemia (FH). In certain embodiments, the patients who are treated or treatable by the methods of the present invention are patients who are diagnosed with (or otherwise known to have), homozygous FH (hoFH) or heterozygous FH (heFH), or at risk for developing abnormally high lipid and/or lipoprotein levels associated with homozygous FH (hoFH) or heterozygous FH (heFH).

The present invention also provides pharmaceutical compositions comprising a PCSK9 inhibitor and an ANGPTL3 inhibitor for use in treating a patient who is non-responsive to, inadequately controlled by, or intolerant to treatment with a standard lipid modifying therapy, such as a statin. The statin may be selected from the group consisting of atorvastatin (LIPITOR®), pitavastatin (LIVALO®), lovastatin (MEVACOR®), simvastatin (ZOCOR®), pravastatin (PRAVACHOL®) fluvastatin (LESCOL®) and rosuvastatin (CRESTOR®). Other standard lipid lowering agents that may be used in patients suffering from hypercholesterolemia, include, but are not limited to, fibrates, niacin, bile acid sequestrants, ezetimibe (ZETIA®), lomitapide (JUZTAPID™), phytosterols, orlistat (XENICAL®).

Exemplary PCSK9 inhibitors, or ANGPTL3 inhibitors that may be used in the context of the methods of the present invention include, e.g., anti-PCSK9 or anti-ANGPTL3 antibodies, small molecule inhibitors, and scaffold-based, i.e. PCSK9-binding molecules, or ANGPTL3-binding molecules.

In certain embodiments, it is envisioned that the use of the combination of the PCSK9 inhibitor with the ANGPTL3 inhibitor may be sufficiently effective at lowering serum lipid and/or lipoprotein levels, such that the dose of the standard lipid modifying therapy may be reduced to eliminate any untoward effects, or it may be eliminated altogether.

In one embodiment, the methods provide for treating a patient in need thereof with an antibody, or an antigen-binding fragment thereof, that binds specifically to PCSK9 in combination with an antibody, or an antigen-binding fragment thereof, that binds specifically to ANGPTL3. In one embodiment, the PCSK9 antibody is administered to the patient at a dose of about 75 mg at a frequency of once every two weeks. In one embodiment, the PCSK9 antibody is administered to the patient at a dose of about 140 mg at a frequency of once every two weeks. In one embodiment, the PCSK9 antibody is administered to the patient at a dose of about 150 mg at a frequency of once every two or four weeks. In one embodiment, the PCSK9 antibody is administered to the patient at a dose of about 300 mg at a frequency of once every four weeks. In one embodiment, the PCSK9 antibody is administered to the patient at a dose of about 420 mg at a frequency of once every four weeks.

In one embodiment, the PCSK9 antibody is selected from the group consisting of alirocumab, evolocumab, bococizumab, lodelcizumab and ralpancizumab.

In one embodiment, the PCSK9 antibody is alirocumab.

In one embodiment, the antibody, or antigen-binding fragment thereof that binds specifically to PCSK9 comprises the complementary determining regions (CDRs) of a heavy chain variable (HCVR) having the amino acid sequence of SEQ ID NO: 12 and the CDRs of a light chain variable region (LCVR) of SEQ ID NO: 17.

In one embodiment, the antibody, or antigen-binding fragment thereof that binds specifically to PCSK9 comprises a heavy chain CDR1 (HCDR1) having the amino acid sequence of SEQ ID NO: 13, a HCDR2 having the amino acid sequence of SEQ ID NO: 14, a HCDR3 having the amino acid sequence of SEQ ID NO: 15, a light chain CDR1 (LCDR1) having the amino acid sequence of SEQ ID NO: 18, a LCDR2 having the amino acid sequence of SEQ ID NO: 19, and a LCDR3 having the amino acid sequence of SEQ ID NO: 21.

In one embodiment, the antibody, or antigen-binding fragment thereof that binds specifically to PCSK9 comprises a HCVR having the amino acid sequence of SEQ ID NO: 12 and a LCVR having the amino acid sequence of SEQ ID NO: 17.

In one embodiment, the PCSK9 antibody is administered to the patient subcutaneously or intravenously.

In one embodiment, the ANGPTL3 antibody is administered to the patient at a dose of about 150 mg at a frequency of once every week. In one embodiment, the ANGPTL3 antibody is administered to the patient at a dose of about 300 mg at a frequency of once every week. In one embodiment, the ANGPTL3 antibody is administered to the patient at a dose of about 450 mg at a frequency of once every week. In one embodiment, the ANGPTL3 antibody is administered to the patient at a dose of about 300 mg at a frequency of once every two weeks. In one embodiment, the ANGPTL3 antibody is administered to the patient at a dose of about 450 mg at a frequency of once every two weeks. In one embodiment, the ANGPTL3 antibody is administered to the patient at a dose of about 20 mg/kg at a frequency of once every four weeks.

In one embodiment, the ANGPTL3 antibody is evinacumab.

In one embodiment, the antibody, or antigen-binding fragment thereof that binds specifically to ANGPTL3 comprises the complementary determining regions (CDRs) of a heavy chain variable (HCVR) having the amino acid sequence of SEQ ID NO: 2 and the CDRs of a light chain variable region (LCVR) of SEQ ID NO: 3.

In one embodiment, the antibody, or antigen-binding fragment thereof that binds specifically to ANGTL3 comprises a heavy chain CDR1 (HCDR1) having the amino acid sequence of SEQ ID NO: 4, a HCDR2 having the amino acid sequence of SEQ ID NO: 5, a HCDR3 having the amino acid sequence of SEQ ID NO: 6, a light chain CDR1 (LCDR1) having the amino acid sequence of SEQ ID NO: 7, a LCDR2 having the amino acid sequence of SEQ ID NO: 8, and a LCDR3 having the amino acid sequence of SEQ ID NO: 9.

In one embodiment, the antibody, or antigen-binding fragment thereof that binds specifically to ANGPTL3 comprises a HCVR having the amino acid sequence of SEQ ID NO: 2 and a LCVR having the amino acid sequence of SEQ ID NO: 3.

In one embodiment, the ANGPTL3 antibody is administered to the patient subcutaneously or intravenously.

In one embodiment, the administration of the PCSK9 antibody in combination with the ANGPTL3 antibody results in an additive effect on lowering the blood level of LDL-C, non-HDL-C and total cholesterol, but has no effect on blood levels of HDL-C.

In one embodiment, the administration of the PCSK9 antibody in combination with the ANGPTL3 antibody results in a synergistic effect on lowering the blood level of LDL-C, non-HDL-C and total cholesterol, but has no effect on blood levels of HDL-C.

In one embodiment, the administration of the PCSK9 antibody in combination with the ANGPTL3 antibody results in lowering one or more of the following parameters:

(a) a reduction in serum total cholesterol (TC) level;
(b) a reduction in serum low-density lipoprotein cholesterol (LDL-C) levels; or
(c) a reduction in serum non-high density lipoprotein cholesterol (non-HDL-C) levels;

wherein the reduction of (a), (b), and/or (c) are determined relative to the patient's serum TC level, serum LDL-C levels and/or serum non-HDL-C levels prior to, or at the time of initiation of treatment with the combination of the PCSK9 inhibitor and the ANGPTL3 inhibitor.

Other embodiments of the present invention will become apparent from a review of the ensuing detailed description.

DETAILED DESCRIPTION

Figure 1:
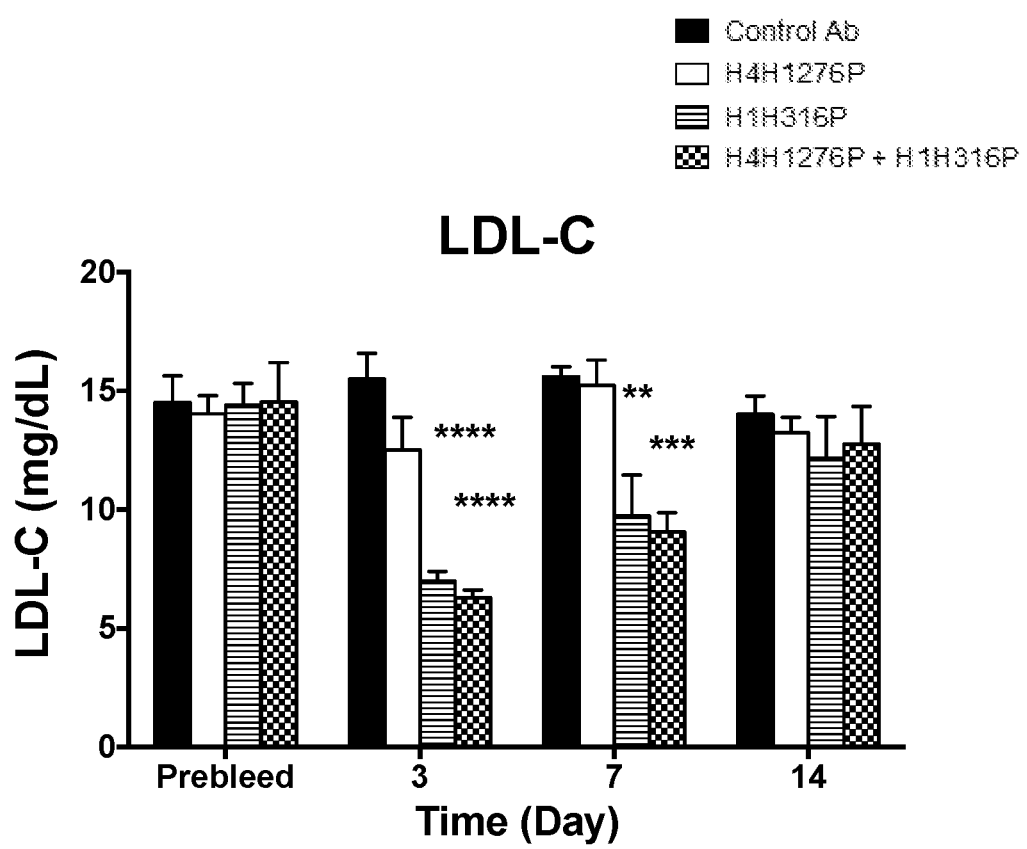
FIG. 1 shows the effect of H4H1276P and H1H316P on LDL-C levels in hyperlipidemic Ldlr$^{-/+}$ mice when used alone or in combination. The mice were placed on a chow diet and were pre-bled five days before the start of the experiment.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating Hyperlipidemias

The present invention relates generally to methods and compositions for reducing lipoprotein levels in patients suffering from hypercholesterolemia, who are non-responsive to, inadequately controlled by, or intolerant to standard lipid modifying therapies (e.g. a statin). In certain embodiments of the invention, treatment with a PCSK9 inhibitor in combination with an ANGPTL3 inhibitor may serve to lower the levels of lipoproteins in these patients to an acceptable range, thereby lowering their risk for development of atherosclerosis, stroke and other cardiovascular diseases. In certain embodiments, the methods described may be used to treat patients suffering from hypercholesterolemia, including heterozygous familial hypercholesterolemia (heFH) and/or homozygous familial hypercholesterolemia (hoFH), in the event that these patients are non-responsive to, inadequately controlled by, or intolerant to standard lipid modifying therapies.

As used herein, the term "lipoprotein" means a biomolecular particle containing both protein and lipid. Examples of lipoproteins include, e.g., low density lipoprotein (LDL), high-density lipoprotein (HDL), very low density lipoprotein (VLDL), intermediate density lipoprotein (IDL), and lipoprotein (a) (Lp(a)).

The present invention, according to certain embodiments, includes methods for treating patients who are non-responsive to, inadequately controlled by, or intolerant to standard lipid modifying therapy. As used herein, a particular patient who is "non-responsive to, inadequately controlled by, or intolerant to, standard lipid modifying therapy" is determined by a physician, physician's assistant, diagnostician, or other medical professional on the basis of the level of one or more lipoproteins (e.g., LDL-C and/or non-HDL-C) measured or otherwise detected in the serum of the patient after treatment with the standard lipid modifying agent. The physician, physician's assistant, diagnostician, or other medical professional can also determine if the patient is intolerant to standard lipid modifying therapies based on the side effect profile of the standard lipid modifying therapies, which the patient may experience, including, but not limited to, muscle aches, tenderness or weakness (myalgia), headache, skin flushing, difficulty sleeping, abdominal cramping, bloating, diarrhea, constipation, rash, nausea, or vomiting. A patient who is non-responsive to, inadequately controlled by, or intolerant to standard lipid modifying therapy may also be determined or influenced by other factors such as the patient's family history, medical background, current therapeutic treatment status, as well as generally accepted or prevailing lipoprotein targets adopted by national medical associations and physicians' groups. For example, in certain contexts, if a patient is undergoing therapy with a standard lipid modifying agent, and exhibits an LDL-C level of greater than or equal to about 70 mg/dL, this indicates that the patient is "non-responsive to, or inadequately controlled by, or intolerant to standard lipid modifying therapy" and may benefit by treatment using the therapies described herein. In other contexts, if a patient is undergoing therapy with a standard lipid modifying agent, and exhibits an LDL-C level of greater than or equal to about 100 mg/dL, this indicates that the patient is "non-responsive to, inadequately controlled by, or intolerant to standard lipid modifying therapy" and may benefit by treatment using the therapies described herein. In certain contexts, if a patient is undergoing therapy with a standard lipid modifying agent, and exhibits an LDL-C level of greater than or equal to about 150 mg/dL, 200 mg/dL, 250 mg/dL, 300 mg/dL, 400 mg/dL or higher, this indicates that the patient is "non-responsive to, inadequately controlled by, or intolerant to standard lipid modifying therapy" and may benefit by treatment using the therapies described herein. In yet other contexts, whether or not a particular percentage reduction in LDL-C or non-HDL-C level is met, relative to the patient's LDL-C or non-HDL-C level at a particular start point ("baseline") can be used to determine whether the patient has responded to standard lipid modifying therapy or whether that patient is in need of further treatment using the methods and agents of the present invention. For instance, a reduction in LDL-C or non-HDL-C of less than 50% (e.g., less than 40%, less than 35%, less than 30%, less than 25%, etc.) from baseline may signify a need for therapy using the methods and agents of the invention.

The present invention, accordingly, includes methods of treatment comprising administration of one or more doses of a PCSK9 inhibitor combined with one or more doses of an ANGPTL3 inhibitor to a patient, whereby the patient's post-treatment levels of total cholesterol, LDL-C, and/or non-HDL-C are significantly reduced in numbers. For example, the present invention includes therapeutic methods comprising administering one or more doses of a PCSK9 inhibitor and one or more doses of an ANGPTL3 inhibitor to a patient who is undergoing standard lipid modifying therapy, but is non-responsive to such therapy, or is intolerant to such therapy, wherein, after receiving one or more doses of the PCSK9 inhibitor and one or more doses of the ANGPTL3 inhibitor, the patient is able to achieve normal levels of total cholesterol, LDL-C, or non-LDL-C. In certain instances, the patient may be taken off of the standard lipid modifying therapy, or the standard lipid modifying therapy may be continued, but may be administered at lower doses and may be used in combination with the PCSK9 inhibitor and the ANGPTL3 inhibitor, to achieve and/or maintain a particular target lipoprotein level. Alternatively, the patient may be administered the standard lipid modifying therapy at the normal prescribed dose, but the frequency of administration of the lipid modifying therapy may be reduced if the standard lipid modifying therapy is to be administered in conjunction with the combination of the PCSK9 inhibitor and the ANGPTL3 inhibitor. In some instances, the need for treatment with the standard lipid modifying therapy by the patient to achieve and/or maintain a particular target lipoprotein level may be eliminated altogether following administration of one or more doses of the PCSK9 inhibitor in conjunction with the ANGPTL3 inhibitor.

According to certain embodiments, the present invention comprises methods for reducing or eliminating the need for standard lipid modifying therapy, wherein the methods comprise selecting a patient with hyperlipidemia (e.g., hypercholesterolemia) who has been treated with lipid modifying therapy within the last month, the last 2 months, the last 3 months, the last 4 months, the last 5 months, the last 6 months, or for a longer period, and administering one or more doses of a PCSK9 inhibitor in combination with an ANGPTL3 inhibitor to the patient. The methods according to this aspect of the invention result in lowering the level of at least one lipoprotein in the serum of the patient, and consequently allow for a reduction or elimination of the need for treatment with the standard lipid modifying therapy by the patient. For example, in certain embodiments of the present invention, following administration of one or more doses of a PCSK9 inhibitor in combination with an ANGPTL3 inhibitor, the serum LDL-C level of the patient is reduced to less than a defined level (e.g., less than 100 mg/dL or less than 70 mg/dL), or the total cholesterol is lowered to a defined level (e.g. less than 200 mg/dL, or less than 150 mg/dL.

According to certain embodiments, the patient who is treatable by the methods of the present invention has hypercholesterolemia (e.g., a serum LDL-C concentration of greater than or equal to 70 mg/dL, or a serum LDL-C concentration greater than or equal to 100 mg/dL). In certain embodiments, the patient's hypercholesterolemia is inadequately controlled by standard lipid modifying therapy, e.g. statin therapy. For example, the present invention includes methods for treating a patient who is non-responsive, inadequately controlled by, or intolerant to, therapy with a standard lipid modifying therapy, such as a statin, or who has hypercholesterolemia that is inadequately controlled by a daily dose of a statin selected form the group consisting of atorvastatin (including atorvastatin+ezetimibe), rosuvastatin, cerivastatin, pitavastatin, fluvastatin, lovastatin, simvastatin (including simvastatin+ezetimibe), pravastatin, and combinations thereof. The present invention also includes methods for reducing cholesterol, LDL-C, or non-LDL-C in a patient who has hypercholesterolemia and who exhibits statin intolerance or who otherwise experiences adverse or undesirable reaction(s) to statin therapy (e.g., skeletal muscle pain, aches, weakness or cramping [e.g., myalgia, myopathy, rhabdomyolysis, etc.]).

Patient Selection

The present invention includes methods and compositions useful for treating patients who are suffering from hyperlipidemia, who are non-responsive to, inadequately controlled by, or intolerant to, therapy with a standard lipid modifying therapy. The patients who are treatable by the methods of the present invention may also exhibit one or more of additional selection criteria. For example, a patient may be selected for treatment with the methods of the present invention if the patient is diagnosed with or identified as being at risk of developing a hypercholesterolemia condition such as, e.g., heterozygous Familial Hypercholesterolemia (heFH), homozygous Familial Hypercholesterolemia (hoFH), Autosomal Dominant Hypercholesterolemia (ADH, e.g., ADH associated with one or more gain-of-function mutations in the PCSK9 gene), autosomal recessive hypercholesterolemia (ARH, e.g., ARH associated with mutations in LDLRAP1), as well as incidences of hypercholesterolemia that are distinct from Familial Hypercholesterolemia (nonFH). Diagnosis of familial hypercholesterolemia (e.g., heFH or hoFH) can be made by genotyping and/or clinical criteria. For patients who are not genotyped, clinical diagnosis may be based on either the Simon Broome criteria with a criteria for definite FH, or the WHO/Dutch Lipid Network criteria with a score >8 points.

According to certain embodiments, the patient may be selected on the basis of having a history of coronary heart disease (CHD). As used herein a "history of CHD" (or "documented history of CHD") includes one or more of: (i)

acute myocardial infarction (MI); (ii) silent MI; (iii) unstable angina; (iv) coronary revascularization procedure (e.g., percutaneous coronary intervention [PCI] or coronary artery bypass graft surgery [CABG]); and/or (v) clinically significant CHD diagnosed by invasive or non-invasive testing (such as coronary angiography, stress test using treadmill, stress echocardiography or nuclear imaging).

According to certain embodiments, the patient may be selected on the basis of having non-coronary heart disease cardiovascular disease ("non-CHD CVD"). As used herein, "non-CHD CVD" includes one or more of: (i) documented previous ischemic stroke with a focal ischemic neurological deficit that persisted more than 24 hours, considered as being of atherothrombotic origin; (ii) peripheral arterial disease; (iii) abdominal aortic aneurysm; (iv) atherosclerotic renal artery stenosis; and/or (v) carotid artery disease (transient ischemic attacks or >50% obstruction of a carotid artery).

According to certain embodiments, the patient may be selected on the basis of having one or more additional risk factors such as, e.g., (i) documented moderate chronic kidney disease (CKD) as defined by 30≤eGFR<60 mL/min/ 1.73 m2 for 3 months or more; (ii) type 1 or type 2 diabetes mellitus with or without target organ damage (e.g., retinopathy, nephropathy, microalbuminuria); (iii) a calculated 10-year fatal CVD risk SCORE ≥5% (ESC/EAS Guidelines for the management of dyslipidemias, Conroy et al., 2003, Eur. Heart J. 24:987-1003).

According to certain embodiments, the patient may be selected on the basis of having one or more additional risk factors selected from the group consisting of age (e.g., older than 40, 45, 50, 55, 60, 65, 70, 75, or 80 years), race, national origin, gender (male or female), exercise habits (e.g., regular exerciser, non-exerciser), other preexisting medical conditions (e.g., type-II diabetes, high blood pressure, etc.), and current medication status (e.g., currently taking beta blockers, niacin, ezetimibe, fibrates, omega-3 fatty acids, bile acid resins, etc.).

According to certain embodiments of the present invention, the subject who is treatable by the methods of the invention exhibits an elevated level of one or more inflammatory marker. Any marker of systemic inflammation can be utilized for the purposes of the present invention. Suitable inflammatory markers include, without limitation, C-reactive protein, cytokines (e.g., IL-6, IL-8, and/or IL-17), and cellular adhesion molecules (e.g., ICAM-1, ICAM-3, BL-CAM, LFA-2, VCAM-1, NCAM, and PECAM).

According to the present invention, patients may be selected on the basis of a combination of one or more of the foregoing selection criteria or therapeutic characteristics. For example, according to certain embodiments, a patient suitable for treatment with the methods of the present invention, may further be selected on the basis of having heFH or non-FH in combination with: (i) a history of documented CHD, (ii) non-CHD CVD, and/or (iii) diabetes mellitus with target organ damage; such patients may also be selected on the basis of having a serum LDL-C concentration of greater than or equal to 70 mg/dL.

According to certain other embodiments, a patient suitable for treatment with the methods of the present invention, in addition to having hypercholesterolemia that is not adequately controlled by a daily moderate-dose therapeutic statin regimen, may further be selected on the basis of having heFH or non-FH without CHD, or non-CHD CVD, but having either (i) a calculated 10-year fatal CVD risk SCORE ≥5%; or (ii) diabetes mellitus without target organ damage; such patients may also be selected on the basis of having a serum LDL-C concentration of greater than or equal to 100 mg/dL.

According to certain embodiments of the present invention, the subject who is treatable by the methods of the invention is a subject who has familial chylomicronemia syndrome (FCS; also known as lipoprotein lipase deficiency).

According to certain embodiments of the present invention, the subject who is treatable by the methods of the invention is a subject who is undergoing, or has recently undergone, lipoprotein apheresis (e.g., within the last six months, within the last 12 weeks, within the last 8 weeks, within the last 6 weeks, within the last 4 weeks, within the last 2 weeks, etc.).

Administration of a PCSK9 Inhibitor Plus an ANGPTL3 Inhibitor as Add-On Therapy

The present invention includes methods of treatment wherein a patient who is undergoing, or has recently undergone, standard lipid modifying therapy (e.g. a statin) is administered a PCSK9 inhibitor plus an ANGPTL3 inhibitor according to a particular dosing amount and frequency, and wherein the PCSK9 inhibitor and the ANGPTL3 inhibitor are administered as an add-on to the patient's pre-existing lipid modifying therapy (if applicable), such as an add-on to the patient's pre-existing daily therapeutic statin regimen.

For example, the methods of the present invention include add-on therapeutic regimens wherein the PCSK9 inhibitor and the ANGPTL3 inhibitor are administered as add-on therapy to the same stable daily therapeutic statin regimen (i.e., same dosing amount of statin) that the patient was on prior to receiving the PCSK9 and ANGPTL3 inhibitors. In other embodiments, the PCSK9 and ANGPTL3 inhibitors are administered as add-on therapy to a therapeutic statin regimen comprising a statin in an amount that is more than or less than the dose of statin the patient was on prior to receiving the PCSK9 and ANGPTL3 inhibitors. For example, after starting a therapeutic regimen comprising a PCSK9 inhibitor and an ANGPTL3 inhibitor administered at particular dosing frequencies and amounts, the daily dose of statin administered or prescribed to the patient may (a) stay the same, (b) increase, or (c) decrease (e.g., up-titrate or down-titrate) in comparison to the daily statin dose the patient was taking before starting the PCSK9 and ANGPTL3 inhibitors therapeutic regimen, depending on the therapeutic needs of the patient.

Therapeutic Efficacy

The methods of the present invention may result in the reduction in serum levels of one or more lipid components selected from the group consisting of total cholesterol, LDL-C, non-HDL-C, ApoB100, VLDL-C, triglycerides, Lp(a) and remnant cholesterol. For example, according to certain embodiments of the present invention, administration of a PCSK9 inhibitor in combination with an ANGPTL3 inhibitor to a suitable subject will result in a mean percent reduction from baseline in serum low density lipoprotein cholesterol (LDL-C) of at least about 25%, 30%, 40%, 50%, 60%, or greater; a mean percent reduction from baseline in ApoB100 of at least about 25%, 30%, 40%, 50%, 60%, or greater; a mean percent reduction from baseline in non-HDL-C of at least about 25%, 30%, 40%, 50%, 60%, or greater; a mean percent reduction from baseline in total cholesterol of at least about 10%, 15%, 20%, 25%, 30%, 35%, or greater; a mean percent reduction from baseline in VLDL-C of at least about 5%, 10%, 15%, 20%, 25%, 30%, or greater; a mean percent reduction from baseline in triglycerides of at least about 5%, 10%, 15%, 20%, 25%, 30%, 35% or greater; and/or a mean percent reduction from baseline in Lp(a) of at least about 5%, 10%, 15%, 20%, 25%, or greater.

PCSK9 Inhibitors and ANGPTL3 Inhibitors

The methods of the present invention comprise administering to a patient a therapeutic composition comprising a PCSK9 inhibitor and an ANGPTL3 inhibitor.

PCSK9 Inhibitors

As used herein, a "PCSK9 inhibitor" is any agent, which binds to or interacts with human PCSK9 and inhibits the normal biological function of PCSK9 in vitro or in vivo. Non-limiting examples of categories of PCSK9 inhibitors include small molecule PCSK9 antagonists, nucleic acid-based inhibitors of PCSK9 expression or activity (e.g., siRNA or antisense), peptide-based molecules that specifically interact with PCSK9 (e.g., peptibodies), receptor molecules that specifically interact with PCSK9, proteins comprising a ligand-binding portion of an LDL receptor, PCSK9-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, etc., [see, e.g., Boersma and Pluckthun, 2011, *Curr. Opin. Biotechnol.* 22:849-857, and references cited therein]), and anti-PCSK9 aptamers or portions thereof. According to certain embodiments, PCSK9 inhibitors that can be used in the context of the present invention are anti-PCSK9 antibodies or antigen-binding fragments of antibodies that specifically bind human PCSK9.

The term "human proprotein convertase subtilisin/kexin type 9" or "human PCSK9" or "hPCSK9", as used herein, refers to PCSK9 having the nucleic acid sequence shown in SEQ ID NO:22 and the amino acid sequence of SEQ ID NO:23, or a biologically active fragment thereof.

ANGPTL3 Inhibitors

As used herein, an "ANGPTL3 inhibitor" is any agent, which binds to or interacts with human ANGPTL3 and inhibits the normal biological function of ANGPTL3 in vitro or in vivo. Non-limiting examples of categories of ANGPTL3 inhibitors include small molecule ANGPTL3 antagonists, nucleic acid-based inhibitors of ANGPTL3 expression or activity (e.g., siRNA or antisense), peptide-based molecules that specifically interact with ANGPTL3 (e.g., peptibodies), receptor molecules that specifically interact with ANGPTL3, ANGPTL3-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, etc., [see, e.g., Boersma and Pluckthun, 2011, *Curr. Opin. Biotechnol.* 22:849-857, and references cited therein]), and anti-ANGPTL3 aptamers or portions thereof. According to certain embodiments, ANGPTL3 inhibitors that can be used in the context of the present invention are anti-ANGPTL3 antibodies or antigen-binding fragments of antibodies that specifically bind human ANGPTL3.

The term "human angiopoietin-like protein-3" or "human ANGPTL3" or "hANGPTL3", as used herein, refers to ANGPTL3 having the amino acid sequence of SEQ ID NO: 1 (see also NCBI Accession NP_055310), or a biologically active fragment thereof.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term includes antibodies recombinantly produced in a non-human mammal, or in cells of a non-human mammal. The term is not intended to include antibodies isolated from or generated in a human subject.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, or that "specifically binds" ANGPTL3, as used in the context of the present invention, includes antibodies that bind PCSK9, or ANGPTL3, or a portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9, or human ANGPTL3, however, has cross-reactivity to other antigens, such as PCSK9 molecules, or ANGPTL3 molecules from other (non-human) species.

The anti-PCSK9 and the anti-ANGPTL3 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9, and anti-ANGPTL3 antibodies comprising variants of any of the HCVR, LCVR, and/or CDR amino acid sequences disclosed herein having one or more conservative substitutions. For example, the present invention includes the use of anti-PCSK9, and anti-ANGPTL3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain embodiments, the anti-PCSK9 and anti-ANGPTL3 antibodies used in the methods of the present invention are antibodies with pH-dependent binding characteristics. As used herein, the expression "pH-dependent binding" means that the antibody or antigen-binding fragment thereof exhibits "reduced binding to PCSK9 at acidic pH as compared to neutral pH" (for purposes of the present disclosure, both expressions may be used interchangeably), or that the antibody or antigen-binding fragment thereof exhibits "reduced binding to ANGPTL3 at acidic pH as compared to neutral pH" (for purposes of the present disclosure, both expressions may be used interchangeably). For the example, antibodies "with pH-dependent binding characteristics" includes antibodies and antigen-binding fragments thereof that bind either to PCSK9, or to ANGPTL3 with higher affinity at neutral pH than at acidic pH. In certain embodiments, the antibodies and antigen-binding fragments of the present invention bind PCSK9, or ANGPTL3 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies, or the ANGPTL3 antibodies with pH-dependent binding characteristics may possess one or more amino acid variations relative to the parental anti-PCSK9 antibody, or the parental anti-ANGPTL3 antibody. For example, an anti-PCSK9 antibody, or an anti-ANGPTL3 antibody with pH-dependent binding characteristics may contain one or more histidine substitutions or insertions, e.g., in one or more CDRs of a parental anti-PCSK9, or a parental anti-ANGPTL3 antibody. Thus, according to certain embodiments of the present invention, methods are provided comprising administering an anti-PCSK9 antibody and an anti-ANGPTL3 antibody which comprises CDR amino acid sequences (e.g., heavy and light chain CDRs) which are identical to the CDR amino acid sequences of a parental anti-PCSK9 antibody, or parental ANGPTL3 antibody except for the substitution of one or more amino acids of one or more CDRs of the parental antibody with a histidine residue. The anti-PCSK9 antibodies, or anti-ANGPTL3 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody, or a parental anti-ANGPTL3 antibody. For example, the present invention includes the use of anti-PCSK9 antibodies and anti-ANGPTL3 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody, or a parental anti-ANGPTL3 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Non-limiting examples of anti-PCSK9 antibodies that can be used in the context of the present invention include, e.g., alirocumab, evolocumab, bococizumab, lodelcizumab, ralpancizumab, or antigen-binding portions of any of the foregoing antibodies.

A non-limiting example of an anti-ANGPTL3 antibody that can be used in the context of the present invention includes evinacumab.

Preparation of Human Antibodies

Anti-PCSK9 antibodies and anti-ANGPTL3 antibodies can be made according to any method of antibody production/isolation known in the art. For example, antibodies for use in the methods of the present invention may be made by hybridoma technologies, by phage display, by yeast display, etc. Antibodies for use in the methods of the present invention may be, e.g., chimeric antibodies, humanized antibodies, or fully human antibodies.

Methods for generating human antibodies in transgenic mice are known in the art. Any such known methods can be used in the context of the present invention to make human antibodies that specifically bind PCSK9, or ANGPTL3.

For example, using VELOCIMMUNE™ technology (see, for example, U.S. Pat. No. 6,596,541, Regeneron Pharmaceuticals) or any other known method for generating monoclonal antibodies, high affinity chimeric antibodies to PCSK9, or to ANGPTL3 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9, which can be used in the context of the methods of the present invention include antibodies or antigen-binding proteins comprising the six CDRs (HCDR1, HCDR2, HCDR3, LCDR1, LCDR2 and LCDR3) from the heavy and light chain variable region (HCVR/LCVR) amino acid sequence pair comprising SEQ ID NOs: 12/17.

In certain embodiments of the present invention, the anti-PCSK9 antibody, or antigen-binding fragment thereof, that can be used in the methods of the present invention comprises heavy and light chain complementarity determining regions (HCDR1-HCDR2-HCDR3/LCDR1-LCDR2-LCDR3) comprising the amino acid sequences of SEQ ID NOs:13, 14, 15, 18, 19 and 21.

In certain embodiments of the present invention, the anti-PCSK9 antibody, or antigen-binding fragment thereof, that can be used in the methods of the present invention comprises an HCVR having the amino acid sequence of SEQ ID NO:12 and an LCVR having the amino acid sequence of SEQ ID NO:17.

Specific examples of human antibodies or antigen-binding fragments of antibodies that specifically bind ANGPTL3, which can be used in the context of the methods of the present invention include antibodies or antigen-binding proteins comprising the six CDRs (HCDR1, HCDR2, HCDR3, LCDR1, LCDR2 and LCDR3) from the heavy and light chain variable region (HCVR/LCVR) amino acid sequence pair comprising SEQ ID NOs: 2/3.

In certain embodiments of the present invention, the anti-ANGPTL3 antibody, or antigen-binding fragment thereof, that can be used in the methods of the present invention comprises heavy and light chain complementarity determining regions (HCDR1-HCDR2-HCDR3/LCDR1-LCDR2-LCDR3) comprising the amino acid sequences of SEQ ID NOs:4, 5, 6, 7, 8 and 9.

In certain embodiments of the present invention, the anti-ANGPTL3 antibody, or antigen-binding fragment thereof, that can be used in the methods of the present invention comprises an HCVR having the amino acid sequence of SEQ ID NO:2 and an LCVR having the amino acid sequence of SEQ ID NO:3.

Pharmaceutical Compositions and Methods of Administration

The present invention includes methods, which comprise administering a PCSK9 inhibitor to a patient in combination with an ANGPTL3 inhibitor, wherein the PCSK9 inhibitor and the ANGPTL3 inhibitor are contained within the same, or in different pharmaceutical compositions. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Exemplary pharmaceutical formulations comprising anti-PCSK9 antibodies, and/or ANGPTL3 antibodies that can be used in the context of the present invention include any of the formulations as set forth in U.S. Pat. No. 8,795,669 (describing, inter alia, exemplary formulations comprising alirocumab), or in WO2013/166448, or WO2012/168491.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of a PCSK9 inhibitor (e.g., anti-PCSK9 antibody), or an ANGPTL3 inhibitor (e.g., anti-ANGPTL3 antibody) administered to a subject according to the methods of the present invention is, generally, a therapeutically effective amount. As used herein, the phrase "therapeutically effective amount of a PCSK9 inhibitor" means a dose of a PCSK9 inhibitor, when administered in combination with an ANGPTL3 inhibitor, results in a detectable reduction (at least about 5%, 10%, 15%, 20%, 25%, 30%, 35%, 40%, 45%, 50%, 55%, 60%, 65%, 70%, 75%, or more from baseline) in one or more parameters selected from the group consisting of total cholesterol, LDL-C, ApoB100, non-HDL-C, VLDL-C, triglycerides, Lp(a) and remnant cholesterol, or an amount that reduces or eliminates a patient's need for other therapeutic interventions, such as, lipoprotein apheresis, or that reduces a patient's normalized rate of apheresis.

In the case of an anti-PCSK9 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody. According to certain exemplary embodiments of the present invention, a therapeutically effective amount of an anti-PCSK9 antibody is 75 mg, 150 mg or 300 mg (e.g., in the case of alirocumab), or 140 mg or 420 mg (e.g., in the case of evolocumab). Other dosing amounts of PCSK9 inhibitors will be apparent to persons of ordinary skill in the art and are contemplated within the scope of the present invention.

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

The amount of ANGPTL3 inhibitor (e.g., anti-ANGPTL3 antibody) administered to a subject according to the methods of the present invention is, generally, a therapeutically effective amount. As used herein, the phrase "therapeutically effective amount of an ANGPTL3 inhibitor" means a dose of ANGPTL3 inhibitor, when combined with a PCSK9 inhibitor, results in a detectable reduction (at least about 5%, 10%, 15%, 20%, 25%, 30%, 35%, 40%, 45%, 50%, 55%, 60%, 65%, 70%, 75%, or more from baseline) in one or more parameters selected from the group consisting of total cholesterol, LDL-C, ApoB100, non-HDL-C, VLDL-C, triglycerides, Lp(a) and remnant cholesterol, or an amount that prevents or attenuates atherosclerosis in a subject (as described elsewhere herein).

In the case of an anti-ANGPTL3 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-ANGPTL3 antibody. Other dosing amounts of ANGPTL3 inhibitors will be apparent to persons of ordinary skill in the art and are contemplated within the scope of the present invention.

The amount of anti-ANGPTL3 antibody contained within the individual doses may be expressed in terms of milligrams of antibody per kilogram of patient body weight (i.e., mg/kg). For example, the anti-ANGPTL3 antibody may be administered to a patient at a dose of about 0.0001 to about 10 mg/kg of patient body weight.

Combination Therapies

As described elsewhere herein, the methods of the present invention may comprise administering a PCSK9 inhibitor in combination with an ANGPTL3 inhibitor to a patient who is non-responsive to, inadequately controlled by, or intolerant to a standard lipid lowering therapy. In certain embodiments, the need for further administration of the lipid lowering therapy may be eliminated altogether. In certain embodiments, the combined use of the PCSK9 inhibitor with the ANGPTL3 inhibitor may be used in combination with ("on top of") the patient's previously prescribed lipid lowering therapy. For example, in the context of lowering at least one lipid/lipoprotein parameter in a patient suffering from hyperlipidemia (e.g. hypercholesterolemia), wherein the patient is non-responsive to, inadequately controlled by, or intolerant to a standard lipid lowering therapy, a combination of a PCSK9 inhibitor with an ANGPTL3 inhibitor may be administered to a patient in combination with a stable daily therapeutic statin regimen. Exemplary daily therapeutic statin regimens that a PCSK9 inhibitor plus an ANGPTL3 inhibitor may be administered in combination with in the context of the present invention include, e.g., atorvastatin (10, 20, 40 or 80 mg daily), (atorvastatin/ezetimibe 10/10 or 40/10 mg daily), rosuvastatin (5, 10 or 20 mg daily), cerivastatin (0.4 or 0.8 mg daily), pitavastatin (1, 2 or 4 mg daily), fluvastatin (20, 40 or 80 mg daily), simvastatin (5, 10, 20, 40 or 80 mg daily), simvastatin/ezetimibe (10/10, 20/10, 40/10 or 80/10 mg daily), lovastatin (10, 20, 40 or 80 mg daily), pravastatin (10, 20, 40 or 80 mg daily), and combinations thereof. Other lipid modifying therapies that a PCSK9 inhibitor plus an ANGPTL3 inhibitor may be administered in combination with in the context of the present invention include, e.g., (1) an agent which inhibits cholesterol uptake and or bile acid re-absorption (e.g., ezetimibe); (2) an agent which increase lipoprotein catabolism (such as niacin); and/or (3) activators of the LXR transcription factor that plays a role in cholesterol elimination such as 22-hydroxycholesterol.

Non-limiting examples of anti-PCSK9 antibodies that can be used in the context of the present invention include, e.g., alirocumab, evolocumab, bococizumab, lodelcizumab, ralpancizumab, or antigen-binding portions of any of the foregoing antibodies.

A non-limiting example of an ANGPTL3 antibody to be used in the context of the present invention includes evinacumab.

Administration Regimens

According to certain embodiments of the present invention, multiple doses of a PCSK9 inhibitor (i.e., a pharmaceutical composition comprising a PCSK9 inhibitor) and an ANGPTL3 inhibitor (i.e., a pharmaceutical composition comprising an ANGPTL3 inhibitor) may be administered to a subject over a defined time course (e.g., on top of a daily therapeutic statin regimen or other background lipid modifying therapy). The methods according to this aspect of the invention comprise sequentially administering to a subject multiple doses of a PCSK9 inhibitor and an ANGPTL3 inhibitor. As used herein, "sequentially administering" means that each dose of PCSK9 inhibitor and ANGPTL3 inhibitor is administered to the subject at a different point in time, e.g., on different days separated by a predetermined interval (e.g., hours, days, weeks or months). The present invention includes methods which comprise sequentially administering to the patient a single initial dose of a PCSK9 inhibitor and an ANGPTL3 inhibitor, followed by one or more secondary doses of the PCSK9 inhibitor and ANGPTL3 inhibitor, and optionally followed by one or more tertiary doses of the PCSK9 inhibitor and ANGPTL3 inhibitor.

The terms "initial dose," "secondary doses," and "tertiary doses," refer to the temporal sequence of administration of the individual doses of a pharmaceutical composition comprising a PCSK9 inhibitor and the ANGPTL3 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the PCSK9 inhibitor and the ANGPTL3 inhibitor, but generally may differ from one another in terms of frequency of administration. In certain embodiments, however, the amount of PCSK9 inhibitor and the ANGPTL3 inhibitor contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

According to exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule, which is administered to a patient prior to the administration of the very next dose in the sequence with no intervening doses.

The methods according to this aspect of the invention may comprise administering to a patient any number of secondary and/or tertiary doses of a PCSK9 inhibitor and ANGPTL3 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2, 4, 6, 8 or more weeks after the immediately preceding dose. Similarly, in embodiments involving multiple tertiary doses, each tertiary dose may be administered at the same frequency as the other tertiary doses. For example, each tertiary dose may be administered to the patient 1 to 2, 4, 6, 8 or more weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human PCSK9

Human anti-PCSK9 antibodies were generated as described in U.S. Pat. No. 8,062,640. The exemplary PCSK9 inhibitor used in the following Example is the human anti-PCSK9 antibody designated "H1H316P," also known as "alirocumab", or "PRAULENT®". H1H316P has the following amino acid sequence characteristics: a heavy chain comprising SEQ ID NO:16 and a light chain comprising SEQ ID NO:20; a heavy chain variable region (HCVR) comprising SEQ ID NO:12 and a light chain variable domain (LCVR) comprising SEQ ID NO:17; a heavy chain complementarity determining region 1 (HCDR1) comprising SEQ ID NO:13, a HCDR2 comprising SEQ ID NO:14, a HCDR3 comprising SEQ ID NO:15, a light chain complementarity determining region 1 (LCDR1) comprising SEQ ID NO:18, a LCDR2 comprising SEQ ID NO:19 and a LCDR3 comprising SEQ ID NO:21.

Example 2

Generation of Human Antibodies to Human ANGPTL3

Human anti-ANGPTL3 antibodies were generated as described in U.S. Pat. No. 9,018,356. The exemplary ANGPTL3 inhibitor used in the following Example is the human anti-ANGPTL3 antibody designated "H4H1276S," also known as "evinacumab." H4H1276S has the following amino acid sequence characteristics: a heavy chain comprising SEQ ID NO:10 and a light chain comprising SEQ ID NO:11; a heavy chain variable region (HCVR) comprising SEQ ID NO:2 and a light chain variable domain (LCVR) comprising SEQ ID NO:3; a heavy chain complementarity determining region 1 (HCDR1) comprising SEQ ID NO:4, a HCDR2 comprising SEQ ID NO:5, a HCDR3 comprising SEQ ID NO:6, a light chain complementarity determining region 1 (LCDR1) comprising SEQ ID NO:7, a LCDR2 comprising SEQ ID NO:8 and a LCDR3 comprising SEQ ID NO:9.

Example 3

In Vivo Effect of Treatment with a Combination of an Anti-hANGPTL3 Antibody and an Anti-PCSK9 Antibody on Circulating Lipid Levels in Hyperlipidemic Ldlr$^{-/+}$ Mice The effect of anti-hANGPTL3 antibody H4H1276 (evinacumab) alone, anti-PCSK9 antibody H1H316P (alirocumab) alone and both antibodies in combination on serum lipids levels was determined in LDLR$^{-/+}$ mice. These mice are hyperlipidemic with majority of their circulating cholesterol found in the form of LDL due to partial deficiency in LDLR, the major receptor for LDL-C uptake.

Figure 2:
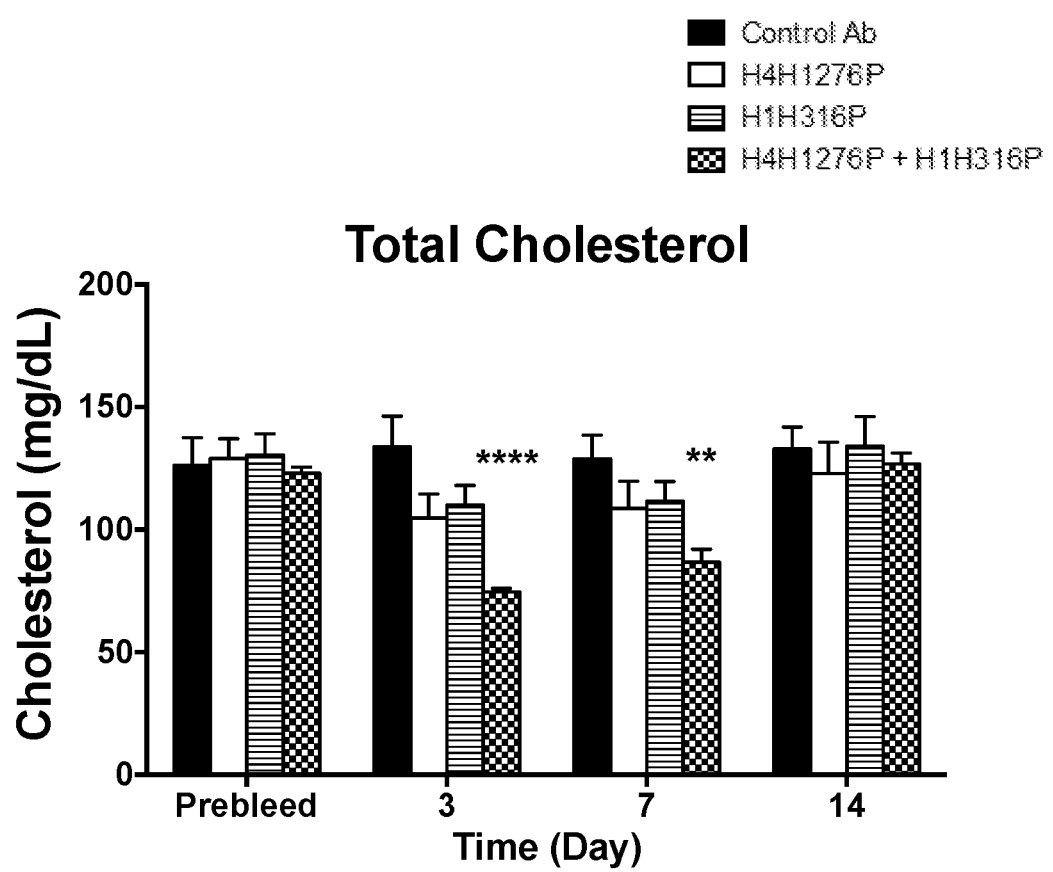
FIG. 2 shows the effect of H4H1276P and H1H316P on total cholesterol levels in hyperlipidemic Ldlr$^{-/+}$ mice when used alone or in combination. The mice were placed on a chow diet and were pre-bled five days before the start of the experiment.
Figure 3:
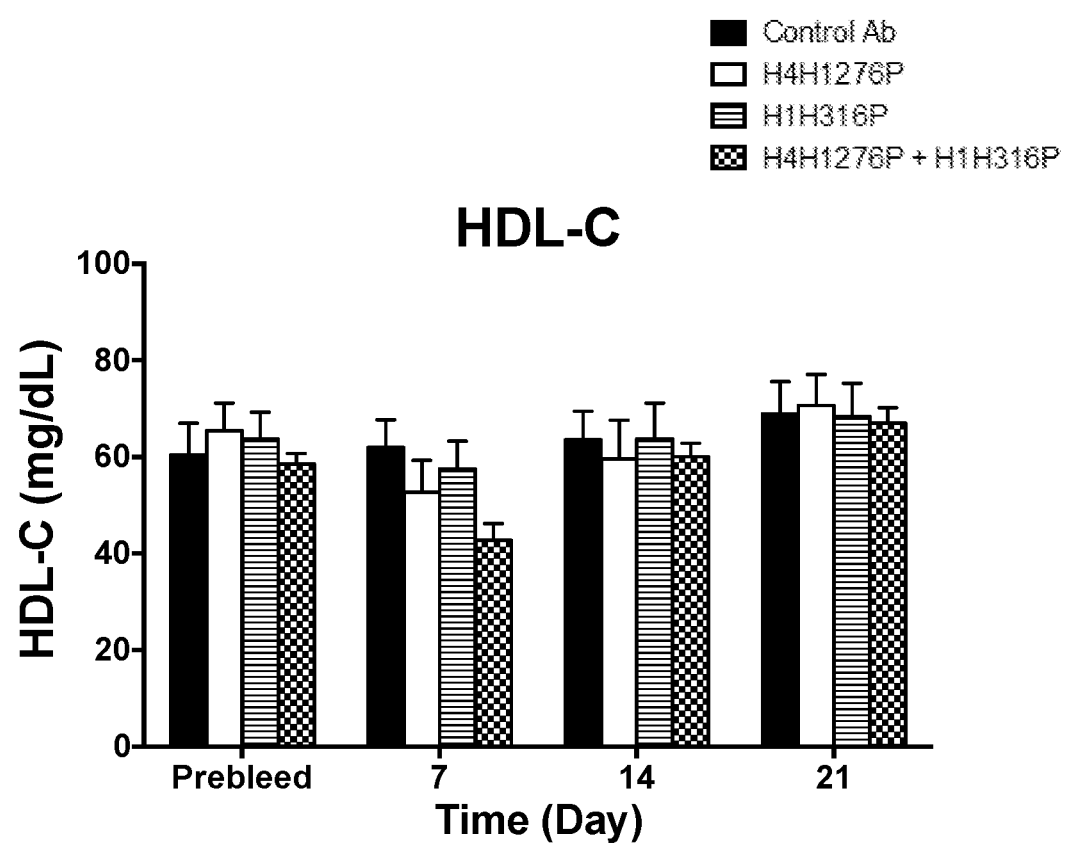
FIG. 3 shows the effect of H4H1276P and H1H316P on HDL-C levels in hyperlipidemic Ldlr$^{-/+}$ mice when used alone or in combination. The mice were placed on a chow diet and were pre-bled five days before the start of the experiment.
Figure 4:
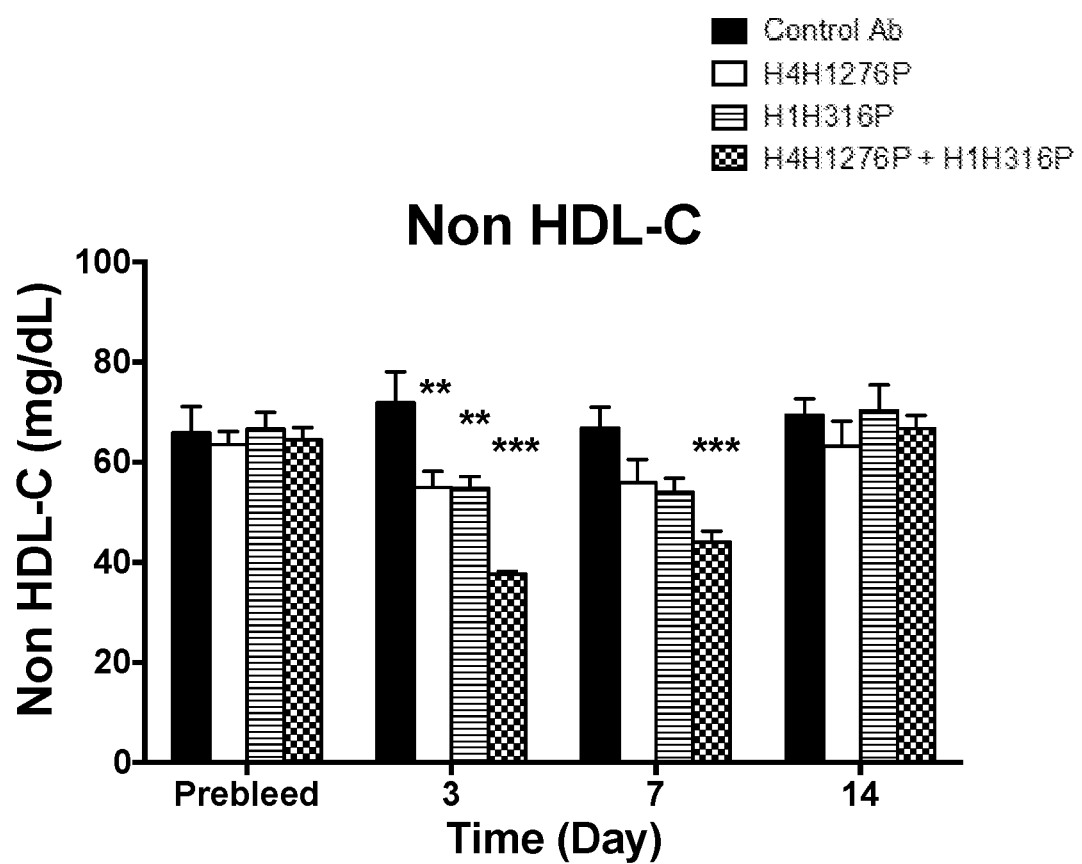
FIG. 4 shows the effect of H4H1276P and H1H316P on Non HDL-C levels in hyperlipidemic Ldlr$^{-/+}$ mice when used alone or in combination. The mice were placed on a chow diet and were pre-bled five days before the start of the experiment.

In the first study, male LDLR$^{-/+}$ mice on chow diet were pre-bled 5 days before the experiment and mice were put into groups of five mice each. The antibodies, H4H1276P, H1H316P, their combination and isotype-matched (hIgG4) control with irrelevant specificity, were administered at a dose of 10 mg/kg each by subcutaneous injection on Day 0 of the study. Mice were bled after 4 hours of fasting on consecutive days after the antibodies injections and serum lipids levels (Total Cholesterol, LDL-C, Non-HDL-C and HDL-C) were determined in the serum by ADVIA® 1800 Chemistry System (Siemens). Averages per group were calculated for each of the time points. Results, expressed as mean±SEM of serum lipids concentration, are shown in FIGS. 1, 2, 3, and 4.

Figure 5:
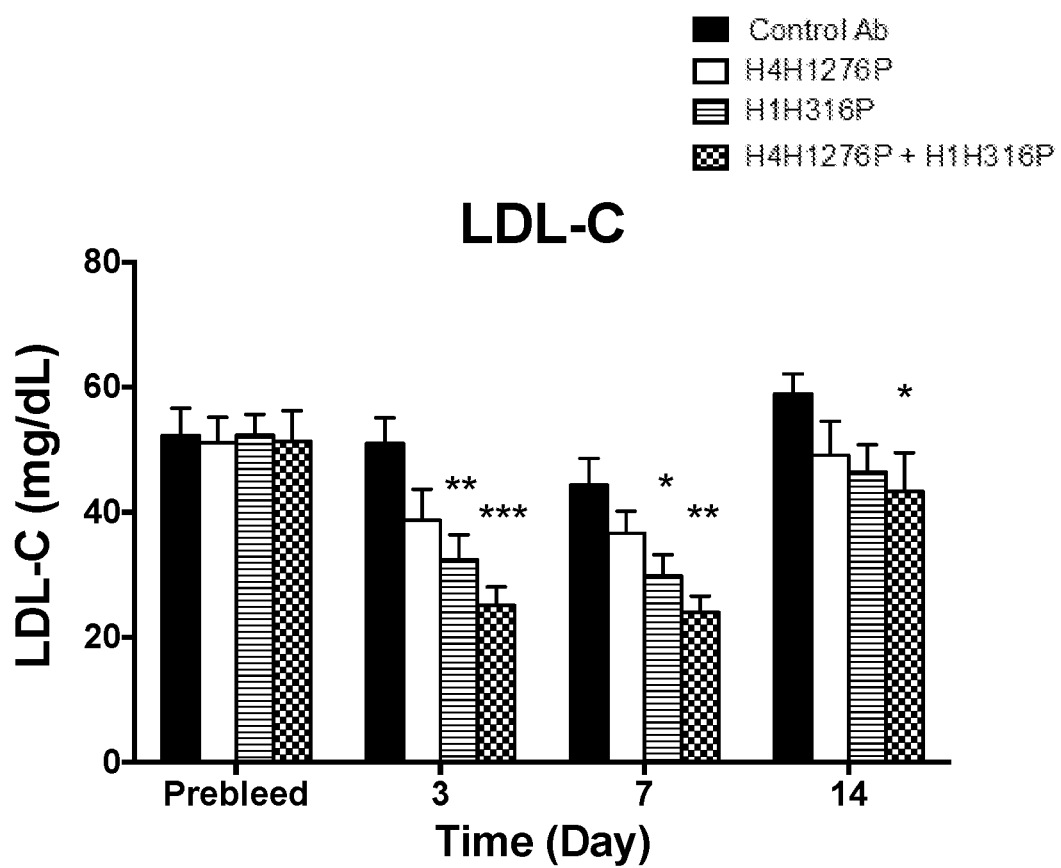
FIG. 5 shows the effect of H4H1276P and H1H316P on LDL-C levels in hyperlipidemic Ldlr$^{-/+}$ mice when used alone or in combination. The mice were placed on a high fat Western diet for 3 weeks prior to treatment and were maintained on this diet throughout the course of the study.
Figure 6:
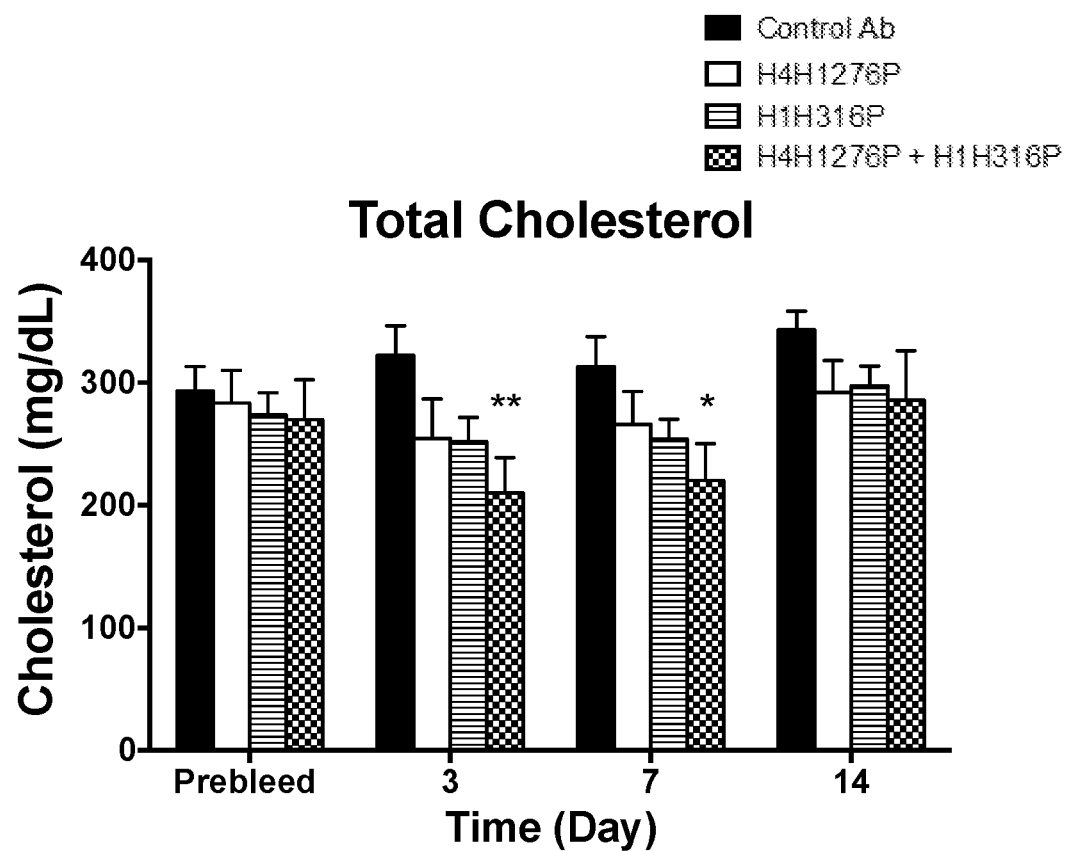
FIG. 6 shows the effect of H4H1276P and H1H316P on total cholesterol levels in hyperlipidemic Ldlr$^{-/+}$ mice when used alone or in combination. The mice were placed on a high fat Western diet for 3 weeks prior to treatment and were maintained on this diet throughout the course of the study.
Figure 7:
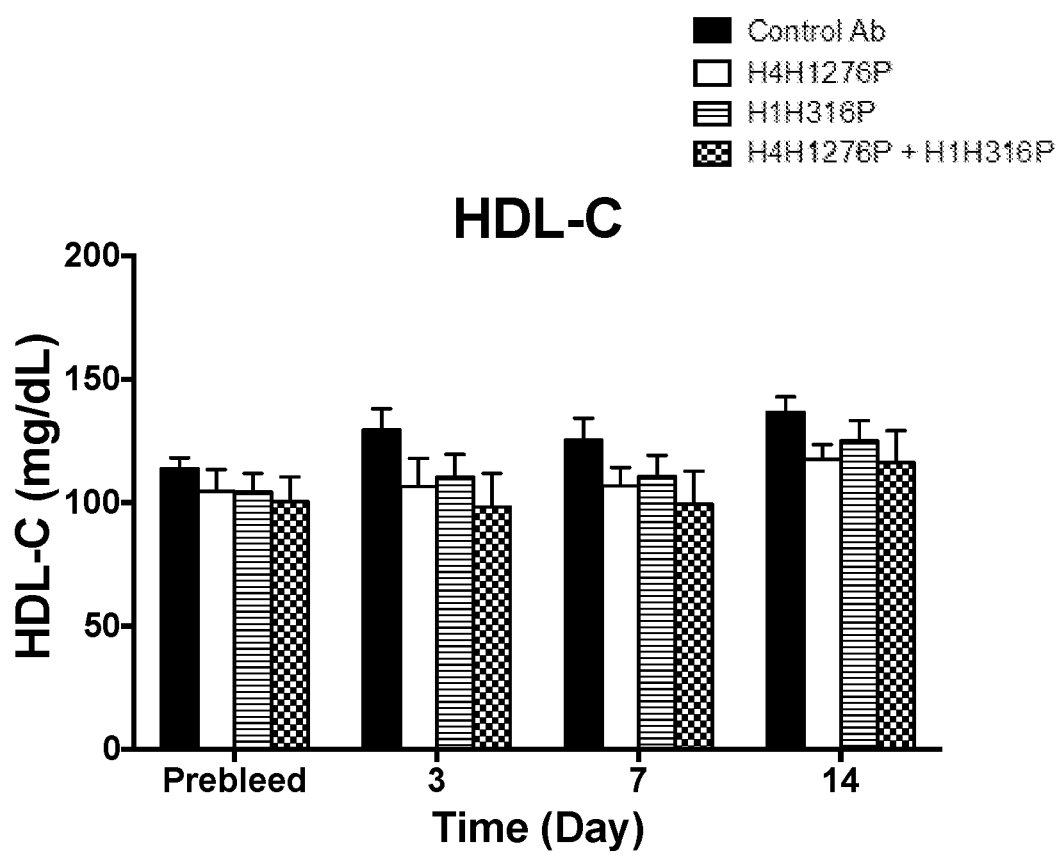
FIG. 7 shows the effect of H4H1276P and H1H316P on HDL-C levels in hyperlipidemic Ldlr$^{-/+}$ mice when used alone or in combination. The mice were placed on a high fat Western diet for 3 weeks prior to treatment and were maintained on this diet throughout the course of the study.
Figure 8:
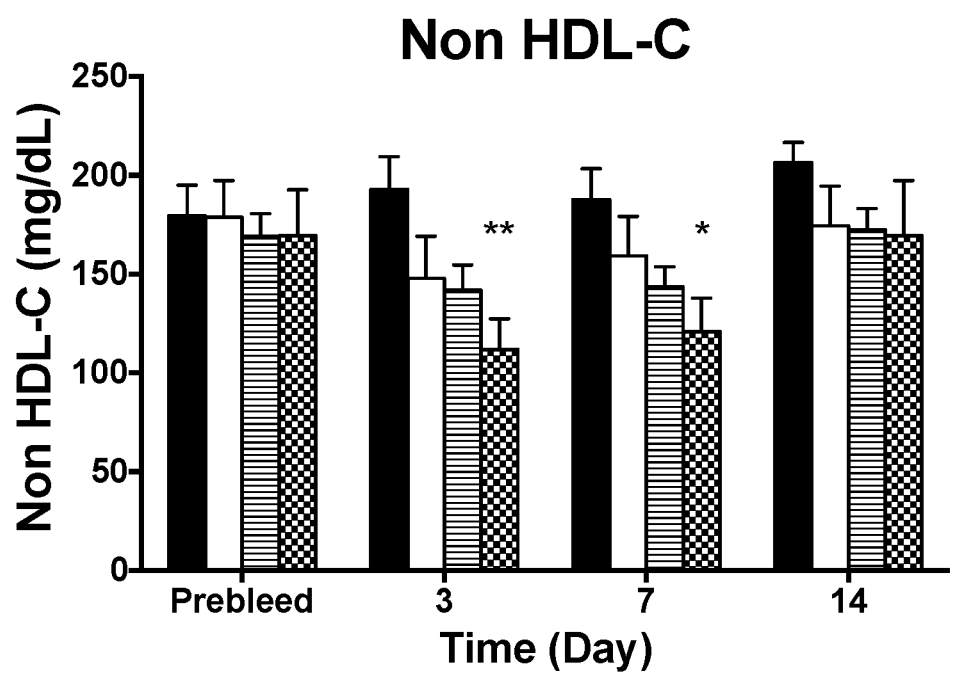
FIG. 8 shows the effect of H4H1276P and H1H316P on Non HDL-C levels in hyperlipidemic Ldlr$^{-/+}$ mice when used alone or in combination. The mice were placed on a high fat Western diet for 3 weeks prior to treatment and were maintained on this diet throughout the course of the study.

In the second study, male LDLR$^{-/+}$ mice were placed on a high fat Western diet for 3 weeks before injection of the antibodies and the mice were fed this diet through the duration of the study. The rest of the study was conducted under the same protocol as for the first study. Results, expressed as mean±SEM of serum lipids concentration, are shown in FIGS. 5, 6, 7 and 8.

Levels of circulating antibodies (Serum Ab) for both studies were determined using a standard ELISA assay. Briefly, plates were coated with a goat anti-human Fc antibody (Sigma-Aldrich) to capture Serum Ab. Serum was then added to the plates and captured antibodies were detected by chemiluminescence using a horseradish peroxidase (HRP) conjugated goat anti-human IgG antibody (Sigma-Aldrich). Results, expressed as mean±SEM are shown in Tables 1A and 1B (first study) and Tables 2A and 2B (second study). Control: Mice that received an isotype-matched Control Ab Results Summary:

The administration of the combination of H1H316P and H4H1276P as single subcutaneous doses to LDLR$^{-/+}$ mice on chow and high fat Western diet lead to a significant reduction in total cholesterol, LDL-C and non-HDL-C and had an additive effect on serum lipid levels when compared to the respective single administration of each antibody.

---

We claim:

1. A method of treating a patient suffering from familial hypercholesterolemia (FH), wherein the patient is non-responsive to, inadequately controlled by, or intolerant to treatment with a standard lipid modifying therapy, the method comprising treating the patient with a combination of a proprotein convertase subtilisin/kexin type 9 (PCSK9) inhibitor and an inhibitor of angiopoietin-like protein 3

(ANGPTL3), wherein the PSCK9 inhibitor is an antibody, or an antigen-binding fragment thereof, that binds specifically to PCSK9, wherein the antibody or antigen-binding fragment thereof that binds specifically to PCSK9 comprises the complementary determining regions (CDRs) of a heavy chain variable (HCVR) having the amino acid sequence of SEQ ID NO: 12 and the CDRs of a light chain variable region (LCVR) of SEQ ID NO: 17, wherein the ANGPTL3 inhibitor is an antibody, or an antigen-binding fragment thereof, that binds specifically to ANGPTL3, wherein the antibody or antigen-binding fragment thereof that binds specifically to ANGPTL3 comprises the complementary determining regions (CDRs) of a heavy chain variable (HCVR) having the amino acid sequence of SEQ ID NO: 2 and the CDRs of a light chain variable region (LCVR) of SEQ ID NO: 3, wherein the patient who is non-responsive to, inadequately controlled by, or intolerant to treatment with a standard lipid modifying therapy exhibits (i) an LDL-C level of greater than or equal to 100 mg/dL despite undergoing the standard lipid modifying therapy or (ii) a reduction in LDL-C or non-HDL-C of less than 50% from baseline despite undergoing the standard lipid modifying therapy.

2. The method of claim 1, wherein the familial hypercholesterolemia (FH) is heterozygous familial hypercholesterolemia (HeFH) or homozygous familial hypercholesterolemia (HoFH).

3. The method of claim 1, wherein the anti-PCSK9 antibody or an antigen-binding fragment thereof is administered to the patient at a dose of about 75 mg at a frequency of once every two weeks.

4. The method of claim 1, wherein the anti-PCSK9 antibody or an antigen-binding fragment thereof is administered to the patient at a dose of about 140 mg at a frequency of once every two weeks.

5. The method of claim 1, wherein the anti-PCSK9 antibody or an antigen-binding fragment thereof is administered to the patient at a dose of about 150 mg at a frequency of once every two weeks, or once every four weeks.

6. The method of claim 1, wherein the anti-PCSK9 antibody or an antigen-binding fragment thereof is administered to the patient at a dose of about 300 mg at a frequency of once every four weeks.

7. The method of claim 1, wherein the anti-PCSK9 antibody or an antigen-binding fragment thereof is administered to the patient at a dose of about 420 mg at a frequency of once every four weeks.

8. The method of claim 1, wherein the anti-PCSK9 antibody is alirocumab.

9. The method of claim 1, wherein the antibody or antigen-binding fragment thereof that binds specifically to PCSK9 comprises a heavy chain CDR1 (HCDR1) having the amino acid sequence of SEQ ID NO: 13, a HCDR2 having the amino acid sequence of SEQ ID NO: 14, a HCDR3 having the amino acid sequence of SEQ ID NO: 15, a light chain CDR1 (LCDR1) having the amino acid sequence of SEQ ID NO: 18, a LCDR2 having the amino acid sequence of SEQ ID NO: 19, and a LCDR3 having the amino acid sequence of SEQ ID NO: 21.

10. The method of claim 1, wherein the antibody or antigen-binding fragment thereof that binds specifically to PCSK9 comprises a HCVR having the amino acid sequence of SEQ ID NO: 12 and a LCVR having the amino acid sequence of SEQ ID NO: 17.

11. The method of claim 1, wherein the anti-PCSK9 antibody or antigen-binding fragment thereof is administered to the patient subcutaneously or intravenously.

12. The method of claim 1, wherein the anti-ANGPTL3 antibody or antigen-binding fragment thereof is administered to the patient at a dose of about 150 mg at a frequency of once every week.

13. The method of claim 1, wherein the anti-ANGPTL3 antibody or antigen-binding fragment thereof is administered to the patient at a dose of about 300 mg at a frequency of once every week.

14. The method of claim 1, wherein the anti-ANGPTL3 antibody or antigen-binding fragment thereof is administered to the patient at a dose of about 450 mg at a frequency of once every week.

15. The method of claim 1, wherein the anti-ANGPTL3 antibody or antigen-binding fragment thereof is administered to the patient at a dose of about 300 mg at a frequency of once every two weeks.

16. The method of claim 1, wherein the anti-ANGPTL3 antibody or antigen-binding fragment thereof is administered to the patient at a dose of about 450 mg at a frequency of once every two weeks.

17. The method of claim 1, wherein the anti-ANGPTL3 antibody or antigen-binding fragment thereof is administered to the patient at a dose of about 20 mg/kg at a frequency of once every four weeks.

18. The method of claim 1, wherein the anti-ANGPTL3 antibody is evinacumab.

19. The method of claim 1, wherein the antibody or antigen-binding fragment thereof that binds specifically to ANGPTL3 comprises a heavy chain CDR1 (HCDR1) having the amino acid sequence of SEQ ID NO: 4, a HCDR2 having the amino acid sequence of SEQ ID NO: 5, a HCDR3 having the amino acid sequence of SEQ ID NO: 6, a light chain CDR1 (LCDR1) having the amino acid sequence of SEQ ID NO: 7, a LCDR2 having the amino acid sequence of SEQ ID NO: 8, and a LCDR3 having the amino acid sequence of SEQ ID NO: 9.

20. The method of claim 1, wherein the antibody or antigen-binding fragment thereof that binds specifically to ANGPTL3 comprises a HCVR having the amino acid sequence of SEQ ID NO: 2 and a LCVR having the amino acid sequence of SEQ ID NO: 3.

21. The method of claim 1, wherein the anti-ANGPTL3 antibody or antigen-binding fragment thereof is administered to the patient subcutaneously or intravenously.

22. The method of claim 1, wherein the treating with a combination of a PCSK9 inhibitor and an inhibitor of ANGPTL3 results in lowering one or more of the following parameters:
  (a) a reduction in serum total cholesterol (TC) level;
  (b) a reduction in serum low-density lipoprotein cholesterol (LDL-C) level; and
  (c) a reduction in serum non-high density lipoprotein cholesterol (non-HDL-C) level
  in the patient, wherein the reduction of (a), (b), and/or (c) is determined relative to the patient's serum TC level, serum LDL-C level, and/or serum non-HDL-C level prior to, or at the time of initiation of, treatment with the combination of the PCSK9 inhibitor and the ANGPTL3 inhibitor.

23. The method of claim 18, wherein the anti-ANGPTL3 antibody is administered to the patient at a dose of about 0.0001 to about 20 mg/kg at a frequency of once every four weeks.

24. The method of claim 23, wherein the anti-ANGPTL3 antibody is administered to the patient at a dose of about 15 mg/kg at a frequency of once every four weeks.

25. The method of claim 24, wherein the anti-ANGPTL3 antibody is administered to the patient by intravenous infusion.

* * * * *